(12) United States Patent
Gregorio et al.

(10) Patent No.: US 7,056,123 B2
(45) Date of Patent: Jun. 6, 2006

(54) INTERFACE APPARATUS WITH CABLE-DRIVEN FORCE FEEDBACK AND GROUNDED ACTUATORS

(75) Inventors: Pedro Gregorio, Verdun (CA); Neil T. Olien, Montreal (CA); David W. Bailey, Menlo Park, CA (US); Steven P. Vassallo, Redwood City, CA (US)

(73) Assignee: Immersion Corporation, San Jose, CA (US)

( * ) Notice: Subject to any disclaimer, the term of this patent is extended or adjusted under 35 U.S.C. 154(b) by 206 days.

(21) Appl. No.: 10/196,563

(22) Filed: Jul. 15, 2002

(65) Prior Publication Data

US 2003/0068607 A1 Apr. 10, 2003

Related U.S. Application Data

(60) Provisional application No. 60/305,957, filed on Jul. 16, 2001.

(51) Int. Cl.
*G09B 23/28* (2006.01)

(52) U.S. Cl. .................................... 434/272; 434/262

(58) Field of Classification Search ................ 434/262, 434/265, 267, 270, 271, 272, 273, 274, 275
See application file for complete search history.

(56) References Cited

U.S. PATENT DOCUMENTS

| 2,972,140 | A | 2/1961 | Hirsch |
|---|---|---|---|
| 3,157,853 | A | 11/1964 | Hirsch |
| 3,220,121 | A | 11/1965 | Cutler |
| 3,497,668 | A | 2/1970 | Hirsch |
| 3,517,446 | A | 6/1970 | Cortyon et al. |
| 3,623,064 | A | 11/1971 | Kagan |
| 3,775,865 | A | 12/1973 | Shepherd |
| 3,902,687 | A | 9/1975 | Hightower |
| 3,903,614 | A | 9/1975 | Diamond et al. |
| 3,911,416 | A | 10/1975 | Feder |

(Continued)

FOREIGN PATENT DOCUMENTS

| EP | 0349086 | 1/1990 |
|---|---|---|
| JP | 01-003664 | 7/1990 |
| JP | H2-185278 | 7/1990 |
| JP | H4-8381 | 1/1992 |
| JP | 02-109714 | 1/1992 |

(Continued)

OTHER PUBLICATIONS

"Taking a Joystick Ride", Computer Currerits, Tim Scannell, Nov. 1994, Boston Edition, vol. 9 No. 11.

(Continued)

*Primary Examiner*—Kurt Fernstrom
(74) *Attorney, Agent, or Firm*—Thelen Reid & Priest LLP; David B. Ritchie

(57) ABSTRACT

A system for providing realistic sensation within a simulation system by providing tactile (haptic) feedback to a user. The system includes an engageable practice tool that the user engages and a mechanical simulation apparatus coupled to the practice tool. The mechanical simulation apparatus includes a ground member, a mechanical linkage rotatably coupled to the ground member, a linear axis member coupled to the practice tool and the mechanical linkage, at least four actuators coupled to the ground member, sensors for sensing movement of the actuators, and at least three cables in contact with the at least four actuators and coupled to the mechanical linkage. An interface device is coupled to the simulation apparatus and a host computer is coupled to the interface device for implementing an application program. The application program provides signals for the actuators to move the cables and thereby move the mechanical linkage.

23 Claims, 22 Drawing Sheets

U.S. PATENT DOCUMENTS

| | | | |
|---|---|---|---|
| 4,127,752 A | | 11/1978 | Lowthorp |
| 4,160,508 A | | 7/1979 | Salisbury |
| 4,228,386 A | * | 10/1980 | Griffith |
| 4,236,325 A | | 12/1980 | Hall et al. |
| 4,262,549 A | | 4/1981 | Schwellenbach |
| 4,333,070 A | | 6/1982 | Barnes |
| 4,464,117 A | | 8/1984 | Foerst |
| 4,484,191 A | | 11/1984 | Vavra |
| 4,513,235 A | | 4/1985 | Acklam et al. |
| 4,581,491 A | | 4/1986 | Boothroyd |
| 4,599,070 A | | 7/1986 | Hladky et al. |
| 4,611,998 A | * | 9/1986 | Ramamurthy ............... 434/265 |
| 4,708,656 A | | 11/1987 | De Vries et al. |
| 4,712,971 A | * | 12/1987 | Fyler |
| 4,713,007 A | | 12/1987 | Alban |
| 4,791,934 A | | 12/1988 | Brunnett |
| 4,794,392 A | | 12/1988 | Selinko |
| 4,879,668 A | | 11/1989 | Cline et al. |
| 4,885,565 A | | 12/1989 | Embach |
| 4,891,764 A | | 1/1990 | McIntosh |
| 4,907,970 A | * | 3/1990 | Meenan, Jr. |
| 4,930,770 A | | 6/1990 | Baker |
| 4,934,694 A | | 6/1990 | McIntosh |
| 4,961,267 A | * | 10/1990 | Herzog |
| 5,019,761 A | | 5/1991 | Kraft |
| 5,022,384 A | | 6/1991 | Freels |
| 5,022,407 A | | 6/1991 | Horch et al. |
| 5,035,242 A | | 7/1991 | Franklin |
| 5,038,089 A | | 8/1991 | Szakaly |
| 5,078,152 A | | 1/1992 | Bond |
| 5,086,401 A | | 2/1992 | Glassman et al. |
| 5,156,363 A | * | 10/1992 | Cizewski et al. |
| 5,165,897 A | | 11/1992 | Johnson |
| 5,175,459 A | | 12/1992 | Danial et al. |
| 5,186,695 A | | 2/1993 | Mangseth et al. |
| 5,212,473 A | | 5/1993 | Louis |
| 5,240,417 A | | 8/1993 | Smithson et al. |
| 5,251,127 A | | 10/1993 | Raab |
| 5,271,290 A | | 12/1993 | Fischer |
| 5,275,174 A | | 1/1994 | Cook |
| 5,283,970 A | | 2/1994 | Aigner |
| 5,299,288 A | | 3/1994 | Glassman et al. |
| 5,299,810 A | | 4/1994 | Pierce |
| 5,309,140 A | | 5/1994 | Everett, Jr. |
| 5,334,027 A | | 8/1994 | Wherlock |
| 5,382,885 A | | 1/1995 | Salcudean et al. |
| 5,397,323 A | | 3/1995 | Taylor et al. |
| 5,403,192 A | * | 4/1995 | Kleinwaks et al. ......... 434/272 |
| 5,436,542 A | * | 7/1995 | Petelin et al. |
| 5,436,622 A | | 7/1995 | Gutman et al. |
| 5,437,607 A | | 8/1995 | Taylor |
| 5,445,166 A | | 8/1995 | Taylor |
| 5,466,213 A | | 11/1995 | Hogan |
| 5,547,382 A | | 8/1996 | Yamasaki |
| 5,575,761 A | | 11/1996 | Hajianpour |
| 5,576,727 A | * | 11/1996 | Rosenberg et al. |
| 5,584,700 A | * | 12/1996 | Feldman et al. |
| 5,587,937 A | * | 12/1996 | Massie et al. |
| 5,623,582 A | | 4/1997 | Rosenberg |
| 5,625,576 A | * | 4/1997 | Massie et al. |
| 5,690,582 A | | 11/1997 | Ulrich et al. |
| 5,701,140 A | * | 12/1997 | Rosenberg et al. |
| 5,724,264 A | * | 3/1998 | Rosenberg et al. |
| 5,731,804 A | * | 3/1998 | Rosenberg |
| 5,766,016 A | | 6/1998 | Sinclair et al. ............ 434/262 |
| 5,785,630 A | | 7/1998 | Bobick et al. |
| 5,800,178 A | * | 9/1998 | Gillio ........................ 434/262 |
| 5,800,179 A | | 9/1998 | Bailey |
| 5,808,665 A | * | 9/1998 | Green |
| 5,816,105 A | * | 10/1998 | Adelstein |
| 5,828,197 A | | 10/1998 | Martin et al. |
| 5,880,714 A | * | 3/1999 | Rosenberg et al. |
| 5,898,599 A | * | 4/1999 | Massie et al. |
| 6,020,875 A | * | 2/2000 | Moore et al. |
| 6,024,576 A | * | 2/2000 | Bevirt et al. |
| 6,037,927 A | | 3/2000 | Rosenberg |
| 6,046,727 A | * | 4/2000 | Rosenberg et al. |
| 6,074,213 A | * | 6/2000 | Hon ........................... 434/262 |
| 6,078,876 A | * | 6/2000 | Rosenberg et al. |
| 6,088,020 A | * | 7/2000 | Mor ........................... 345/156 |
| 6,100,874 A | * | 8/2000 | Schena et al. |
| 6,104,382 A | * | 8/2000 | Martin et al. |
| 6,106,301 A | * | 8/2000 | Merril ........................ 434/262 |
| 6,111,577 A | | 8/2000 | Zilles et al. |
| 6,125,337 A | * | 9/2000 | Rosenberg et al. |
| 6,160,489 A | | 12/2000 | Perry et al. |
| 6,219,034 B1 | | 4/2001 | Elbing et al. |
| 6,246,390 B1 | | 6/2001 | Rosenberg |
| 6,323,837 B1 | | 11/2001 | Rosenberg |
| 6,380,925 B1 | * | 4/2002 | Martin et al. |
| 6,400,352 B1 | * | 6/2002 | Bruneau et al. |
| 6,422,941 B1 | | 7/2002 | Thorner et al. |
| 6,654,000 B1 | * | 11/2003 | Rosenberg ................... 345/156 |
| 6,705,871 B1 | * | 3/2004 | Bevirt et al. ................. 434/262 |
| 2001/0016804 A1 | | 8/2001 | Cunningham et al. |

FOREIGN PATENT DOCUMENTS

| | | |
|---|---|---|
| JP | 04-007371 | 8/1993 |
| JP | H5-192449 | 8/1993 |
| JP | H7-24147 | 1/1995 |
| JP | 05-193862 | 1/1995 |
| WO | WO 09216141 | 10/1992 |
| WO | WO 9426167 | 11/1994 |
| WO | WO 9510080 | 4/1995 |
| WO | WO 9639944 | 12/1996 |

OTHER PUBLICATIONS

"Coaxial Control Shaker Part No. C–25502," Safe Flight Instrument Corporation, 26 pages, Jul. 1, 1967; Revised Jan. 28, 2002.

Baigrie, "Electric Control Loading—A Low Cost, High Performance Alternative," Proceedings, pp. 247–254, Nov. 6–8, 1990.

Iwata, "Pen–based Haptic Virtual Environment," 0–7803–1363–1/93 IEEE, pp 287–292, 1993.

Russo, "The Design and Implementation of a Three Degree of Freedom Force Output Joystick," MIT Libraries Archives Aug. 14, 1990, pp. 1–131, May 1990.

Brooks et al., "Hand Controllers for Teleoperation—A State–of–the–Art Technology Survey and Evaluation," JPL Publication 85–11; NASA–CR–175890; N85–28559, pp. 1–84, Mar. 1, 1985.

Jones et al., "A perceptual analysis of stiffness," ISSN 0014–4819 Springer International (Springer–Verlag); Experimental Brain Research, vol. 79, No. 1, pp. 150–156, 1990.

Burdea et al., "Distributed Virtual Force Feedback, Lecture Notes for Workshop on Force Display in Virtual Environments and its Application to Robotic Teleoperation," 1993 IEEE International Conference on Robotics and Automation, pp. 25–44, May 2, 1993.

Snow et al., " Model–X Force–Reflecting–Hand–Controller," NT Control No. MPO–17851; JPL Case No. 5348, pp. 1–4, Jun. 16, 1989.

Ouh–Young, "Force Display in Molecular Docking," Order No. 9034744, p. 1–369, 1990.

Tadros, "Control System Design for a Three Degree of Freedom Virtual Environment Simulator Using Motor/Brake Pair Actuators", MIT Archive © Massachusetts Institute of Technology, pp. 1–88, Feb. 1990.

Caldwell, et al., "Enhanced Tactile Feedback (Tele–Taction) Using a Multi–Functional Sensory System," 1050–4729/93, pp. 955–960, 1993.

Adelstein, "Design and Implementation of a Force Reflecting Manipulandum for Manual Control research," DSC–Vol. 42, Advances in Robotics, Edited by H. Kazerooni, pp. 1–12, 1992.

Gotow et al., "Controlled Impedance Test Apparatus for Studying Human Interpretation of Kinesthetic Feedback," WA11–11:00, pp. 332–337.

Stanley et al., "Computer Simulation of Interacting Dynamic Mechanical Systems Using Distributed Memory Parallel Processors," DSC–vol. 42, Advances in Robotics, pp. 55–61, ASME 1992.

Russo, "Controlling Dissipative Magnetic Particle Brakes in Force Reflective Devices," DSC–vol. 42, Advances in Robotics, pp. 63–70, ASME 1992.

Kontarinis et al., "Display of High–Frequency Tactile Information to Teleoperators," Telemanipulator Technology and Space Telerobotics, Won S. Kim, Editor, Proc. SPIE vol. 2057, pp. 40–50, Sep. 7–9, 1993.

Patrick et al., "Design and Testing of A Non–reactive, Fingertip, Tactile Display for Interaction with Remote Environments," Cooperative Intelligent Robotics in Space, Rui J. deFigueiredo et al., Editor, Proc. SPIE vol. 1387, pp. 215–222, 1990.

Adelstein, "A Virtual Environment System For The Study of Human Arm Tremor," Ph.D. Dissertation, Dept. of Mechanical Engineering, MIT, Jun. 1989.

Bejczy, "Sensors, Controls, and Man–Machine Interface for Advanced Teleoperation," Science, vol. 208, No. 4450, pp. 1327–1335, 1980.

Bejczy, "Generation of Bilateral Force–Reflecting Control of Manipulators," Proceedings Of Fourth CISM–IFToMM, Sep. 8–12, 1981.

McAffee, "Teleoperator Subsystem/Telerobot Demonsdtrator: Force Reflecting Hand Controller Equipment Manual," JPL D–5172, pp. 1–50, A1–A36, B1–B5, C1–C36, Jan. 1988.

Minsky, "Computational Haptics: The Sandpaper System for Synthesizing Texture for a Force–Feedback Display," Ph.D. Dissertation, MIT, Jun. 1995.

Jacobsen et al., "High Performance, Dextrous Telerobotic Manipulator With Force Reflection," Intervention/ROV '91 Conference & Exposition, Hollywood, Florida, May 21–23, 1991.

Shimoga, "Finger Force and Touch Feedback Issues in Dexterous Telemanipulation," Proceedings of Fourth Annual Conference on Intelligent Robotic Systems for Space Expploration, Rensselaer Polytechnic Institute, Sep. 30—Oct. 1, 1982.

IBM Technical Disclosure Bulletin, "Mouse Ball–Actuating Device With Force and Tactile Feedback," vol. 32, No. 9B, Feb. 1990.

Terry et al., "Tactile Feedback In A Computer Mouse," Proceedings of Fouteenth Annual Northeast Bioengineering Conference, University of New Hampshire, Mar. 10–11, 1988.

Howe, "A Force–Reflecting Teleoperated Hand System for the Study of Tactile Sensing in Precision Manipulation," Proceedings of the 1992 IEEE International Conference on Robotics and Automation, Nice, France, May 1992.

Eberhardt et al., "OMAR—A Haptic display for speech perception by deaf and deaf–blind individuals," IEEE Virtual Reality Annual International Symposium, Seattle, WA, Sep. 18–22, 1993.

Rabinowitz et al., "Multidimensional tactile displays: Identification of vibratory intensity, frequency, and contactor area," Journal of The Acoustical Society of America, vol. 82, No. 4, Oct. 1987.

Bejczy et al., "Kinesthetic Coupling Between Operator and Remote Manipulator," International Computer Technology Conference, The American Society of Mechanical Engineers, San Francisco, CA, Aug. 12–15, 1980.

Bejczy et al., "A Laboratory Breadboard System For Dual–Arm Teleoperation," SOAR '89 Workshop, JSC, Houston, TX, Jul. 25–27, 1989.

Ouh–Young, "A Low–Cost Force Feedback Joystick and Its Use in PC Video Games," IEEE Transactions on Consumer Electronics, vol. 41, No. 3, Aug. 1995.

Marcus, "Touch Feedback in Surgery," Proceedings of Virtual Reality and Medicine The Cutting Edge, Sep. 8–11, 1994.

Bejczy, et al., "Universal Computer Control System (UCCS) For Space Telerobots," CH2413–3/87/0000/0318501.00 1987 IEEE, 1987.

Aukstakalnis et al., "Silicon Mirage: The Art and Science of Virtual Reality," ISBN 0–938151–82–7, pp. 129–180, 1992.

Eberhardt et al., "Including Dynamic Haptic Perception by The Hand: System Description and Some Results," DSC–vol. 55–1, Dynamic Systems and Control: vol. 1, ASME 1994.

Gobel et al., "Tactile Feedback Applied to Computer Mice," International Journal of Human–Computer Interaction, vol. 7, No. 1, pp. 1–24, 1995.

Pimentel et al., "Virtual Reality: through the new looking glass," $2^{nd}$ Edition; McGraw–Hill, ISBN 0–07–050167–X, pp. 41–202, 1994.

"Cyberman Technial Specification," Logitech Cyberman SWIFT Supplement, Apr. 5, 1994.

Ouhyoung et al., "The Development of A Low–Cost Force Feedback Joystick and Its Use in the Virtual Reality Environment," Proceedings of the Third Pacific Conference on Computer Graphics and Applications, Pacific Graphics '95, Seoul, Korea, Aug. 21–24, 1995.

Kaczmarek et al., "Tactile Displays," Virtual Environment Technologies.

Scannell, "Taking a Joystick Ride," Computer Currents, Boston Edition, vol. 9, No. 11, Nov. 1994.

Patrick, "Design, Construction, and Testing of a Fingertip Tactile Display for Interaction with Virtual and Remote Environments," *Master of Science Thesis*, MIT, Aug. 1990, archived Nov. 8, 1990.

Calder, "Design of A Force–Feedback Touch–Introducing Actuator For Teleoperator Robot Control," *Bachelor of Science Thesis*, MIT, May 1983, archived Jun. 23, 1983.

Wiker, "Teletouch Display Development: Phase 1 Report," *Technical Report 1230*, Naval Ocean Systems Center, San Diego, Jul. 1988.

Bliss, "Optical–to–Tactile Image Conversion for the Blind," *IEEE Transactions on Man–Machine Systems*, vol. MMS–11, No. 1, Mar. 1970.

Johnson, "Shape–Memory Alloy Tactile Feedback Actuator," *Armstrong Aerospace Medical Research Laboratory*, AAMRL–TR–90–039, Aug., 1990.

Kontarinis et al., "Tactile Display of Vibratory Information in Teleoperation and Virtual Environments," PRESENCE, 4(4):387–402, Harvard Univ., 1995.

Lake, "Cyberman from Logitech," at http://www.ibiblio.org/GameBytes/Issue21/greviews/cyberman.html, 1994.

"Component Maintenance Manual With Illustrated Parts List, Coaxial Control Shaker Part No. C–25502," Safe Flight Instrument Corporation, Revised Jan. 28, 2002 (3 pages).

"Technical Manual Overhaul Instructions With Parts Breakdown, Coaxial Control Shaker Part No. C–25502," Safe Flight Instrument Corporation, Revised Jul. 15, 1980 (23 pages).

Yamakita et al., "Tele–Virtual Reality of Dynamic Mechanical Model," *Proceedings of the 1992 IEEE/RSJ International Conference on Intelligent Robots and Systems*, Raleigh, NC, Jul. 7–10, 1992.

Noll, "Man–Machine Tactile," *SID Journal*, Jul./Aug. 1972 Issue.

Rosenberg, "Virtual Fixtures: Perceptual Overlays Enhance Operator Performance In Telepresence Tasks," *Ph.D. Dissertation*, Stanford University, Jun. 1994.

\* cited by examiner

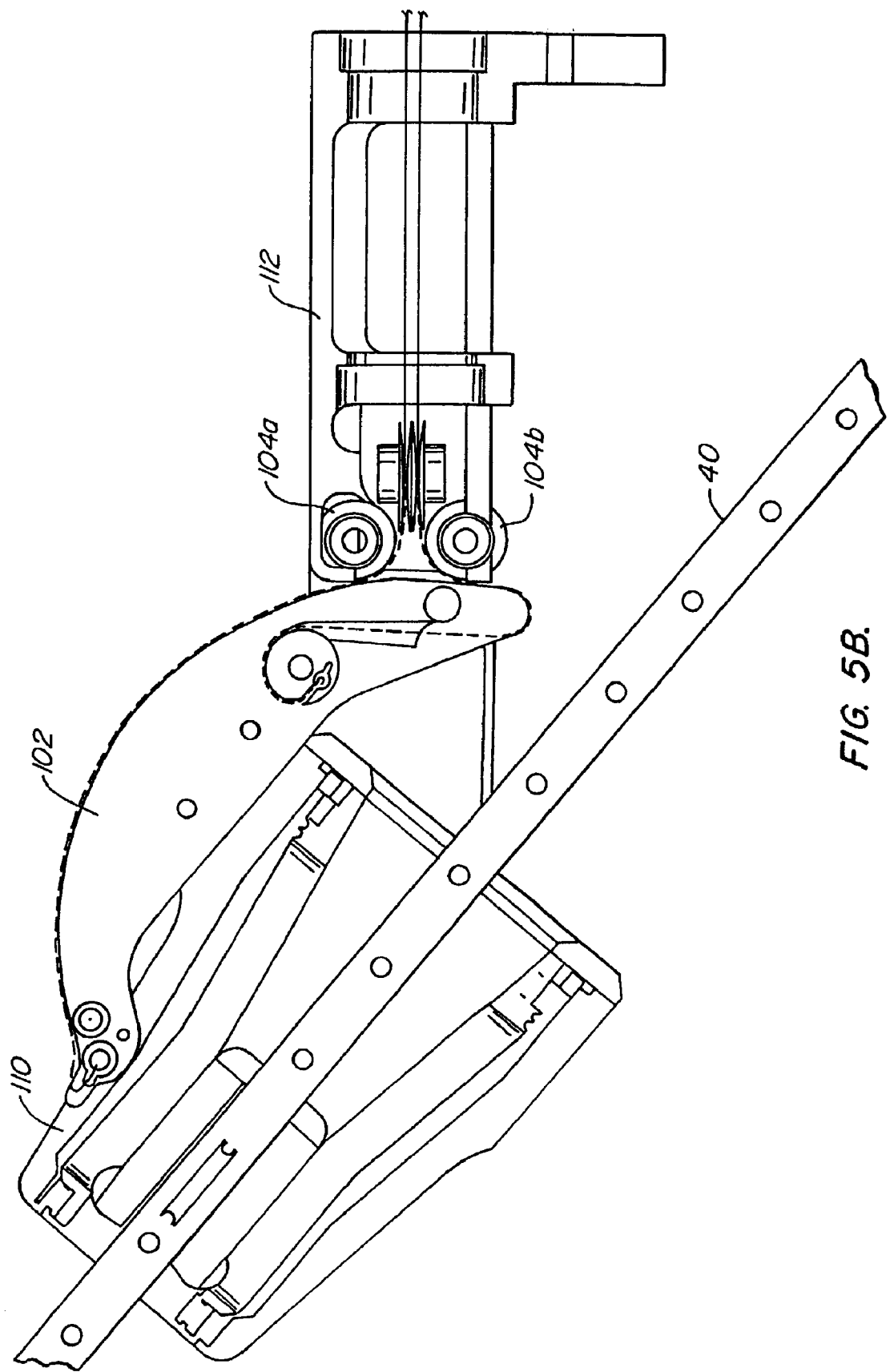

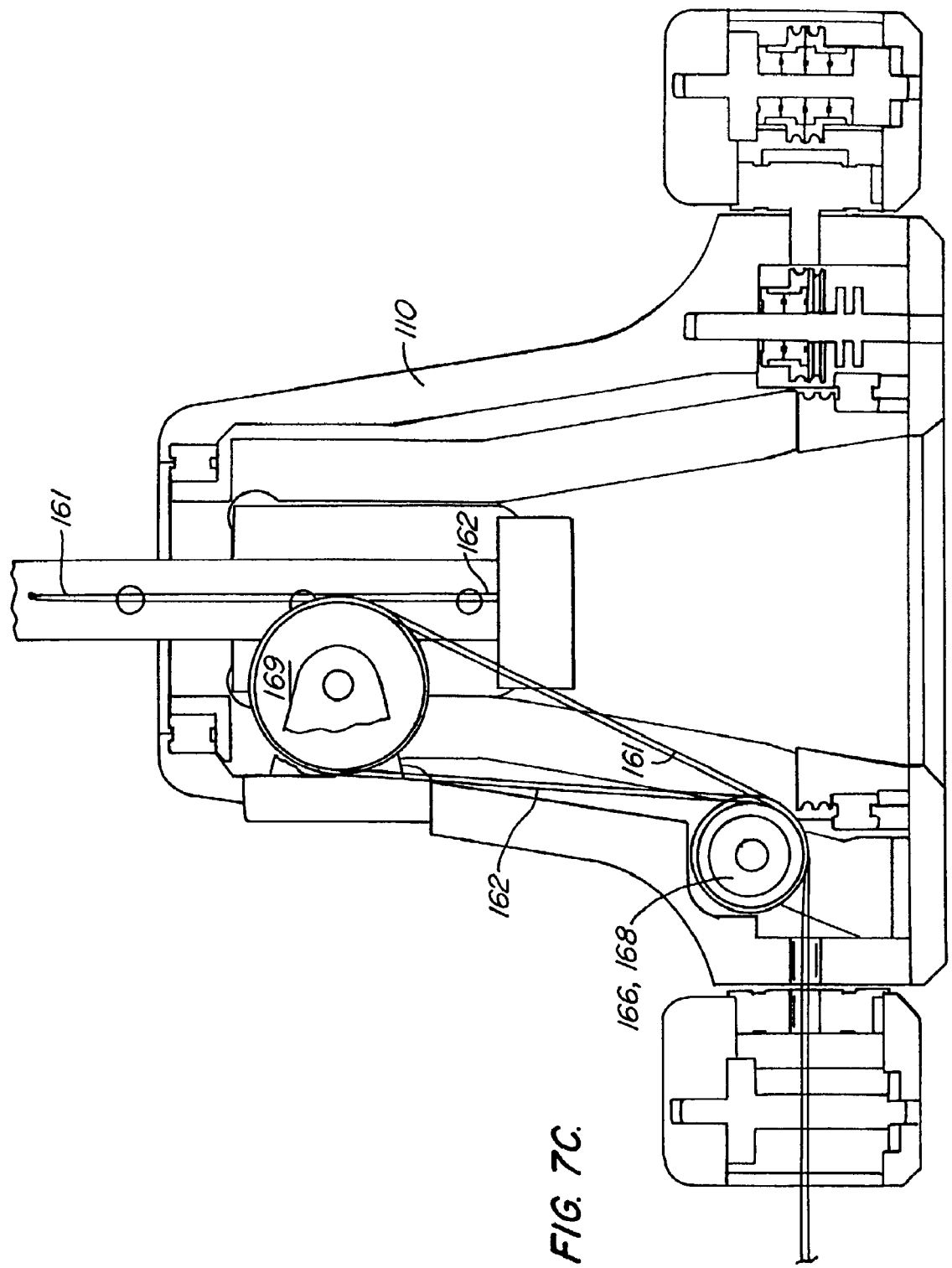

US 7,056,123 B2

INTERFACE APPARATUS WITH CABLE-DRIVEN FORCE FEEDBACK AND GROUNDED ACTUATORS

CROSS-REFERENCES TO RELATED APPLICATIONS

This application claims the benefit of U.S. Provisional Patent Application Ser. No. 60/305,957, filed Jul. 16, 2001, entitled "INTERFACE APPARATUS WITH CABLE-DRIVEN FORCE FEEDBACK AND FOUR GROUNDED ACTUATORS," the contents of which are hereby incorporated in its entirety for all purposes.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present invention relates generally to interface devices between humans and computers, and more particularly to computer interface devices that provide force feedback to the user.

2. Description of the Prior Art

Virtual reality computer systems provide users with the illusion that they are part of a "virtual" environment. A virtual reality system will typically include a computer processor, virtual reality software, and virtual reality I/O devices such as head mounted displays, sensor gloves, three dimensional ("3D") pointers, etc.

Virtual reality computer systems may be used for training. In many fields, such as aviation and vehicle and systems operation, virtual reality systems have been used successfully to allow a user to learn from and experience a realistic "virtual" environment. The appeal of using virtual reality computer systems for training relates, in part, to the ability of such systems to allow trainees the luxury of confidently operating in a highly realistic environment and making mistakes without "real world" consequences. For example, a virtual reality computer system allows a doctor-trainee or other human operator or user to "manipulate" a scalpel or probe within a computer-simulated "body," and thereby perform medical procedures on a virtual patient. In this instance, the I/O device, which is typically a 3D pointer, stylus, or the like, is used to represent a surgical instrument such as a scalpel or probe. As the "scalpel" or "probe" moves within a provided space or structure, results of such movement are updated and displayed in a body image displayed on the screen of the computer system so that the operator gains the experience of performing such a procedure without practicing on an actual human being or a cadaver. In other applications, virtual reality computer systems allow a user to handle and manipulate the controls of complicated and expensive vehicles and machinery for training and/or entertainment purposes.

For virtual reality systems to provide a realistic (and therefore effective) experience for the user, sensory feedback and manual interaction should be as natural as possible. In addition to sensing and tracking a user's manual activity and feeding such information to the controlling computer to provide a 3D visual representation to the user, a human interface mechanism should also provide force or tactile ("haptic") feedback to the user. The need for the user to obtain realistic haptic information is extensive in many kinds of simulation and other applications. For example, in medical/surgical simulations, the "feel" of a probe or scalpel simulator is important as the probe is moved within the simulated body. It would be invaluable to a medical trainee to learn how an instrument moves within a body, how much force is required depending on the operation performed, the space available in a body to manipulate an instrument, etc. Other applications similarly benefit from the realism provided by haptic feedback. A "high bandwidth" interface system, which is an interface that accurately responds to signals having fast changes and a broad range of frequencies as well as providing such signals accurately to a control system, is therefore desirable in these and other applications.

Several existing devices provide multiple degrees of freedom of motion of an instrument or manipulatable object and include haptic feedback. Many of these devices, however, are limited in how many degrees of freedom that forces are provided, and may also be less accurate and realistic than desired for a particular application. Devices having greater realism yet reasonable cost are desired for medical and other virtual simulation applications.

SUMMARY OF THE INVENTION

The present invention provides a system for providing a realistic sensation to a user by providing resistance. The system includes an engageable practice tool that the user engages. A mechanical simulation apparatus is coupled to the practice tool and an interface device is coupled to the simulation device. A host computer is coupled to the interface device for implementing an application program. The application program provides signals for a mechanical simulation apparatus to provide resistance to the practice tool based upon sensed positions of the practice tool.

In accordance with one aspect of the present invention, the practice tool is configured as a practice medical tool.

In accordance with another aspect of the present invention, the interface device is included within the host computer.

In accordance with a further aspect of the present invention, the interface device is separate from the host computer.

In accordance with yet another aspect of the present invention, the interface device comprises a microprocessor local to the mechanical simulation apparatus.

In accordance with a further aspect of the present invention, the system further includes a barrier between the mechanical simulation apparatus and the user.

In accordance with another aspect of the present invention, the practice tool is configured as a laparoscopic tool and includes a trocar.

In accordance with yet another aspect of the present invention, the practice tool is configured as one of a group comprising catheters, hypodermic needles, wires, fiber optic bundles, styluses, joysticks, screw drivers, pool queues and handgrips.

In accordance with yet a further aspect of the present invention, the system includes multiple practice tools.

In accordance with one aspect of the present invention, the mechanical simulation apparatus includes a ground member, a mechanical linkage coupled to the ground member, a linear axis member coupled to the practice tool and the mechanical linkage, at least one actuator coupled to the ground member, and a cable in engagement with at least one actuator and coupled to the mechanical linkage.

In accordance with another aspect of the present invention, the system includes at least four actuators.

In accordance with a further aspect of the present invention, the actuators comprise the DC motors.

In accordance with yet another aspect of the present invention, the system includes at least three cables in various engagement with the at least four actuators.

In accordance with a further aspect of the present invention, at least one sensor is provided that senses movement of the actuators and/or the mechanical linkage.

The present invention also provides a method for providing a realistic sensation to a user by providing resistance. The method includes providing an engageable practice tool coupled to a mechanical simulation apparatus comprising a mechanical linkage, at least one actuator, at least one cable in engagement with the at least one actuator and coupled to the mechanical linkage, and a sensor. The method further includes engaging the tool by the user and applying a force to the practice tool by the user. The position of the tool is sensed with the sensor. The position sensed is provided to a host computer that includes an application program, and a signal is provided from the host computer to the at least one actuator to move the at least one cable and thereby move the mechanical linkage. The signal is based upon the position sensed and the application program.

Other features and advantages of the present invention will be understood upon reading and understanding the description of the preferred exemplary embodiments, found hereinbelow, in conjunction with reference to the drawings, in which like numerals represent like elements.

BRIEF DESCRIPTION OF THE DRAWINGS

FIGS. 5A–5D are side sectional views of the mechanical linkage;

FIGS. 7A–7C are additional sectional perspective views of the mechanical linkage;

DESCRIPTION OF SPECIFIC EXEMPLARY EMBODIMENTS

Figure 1:
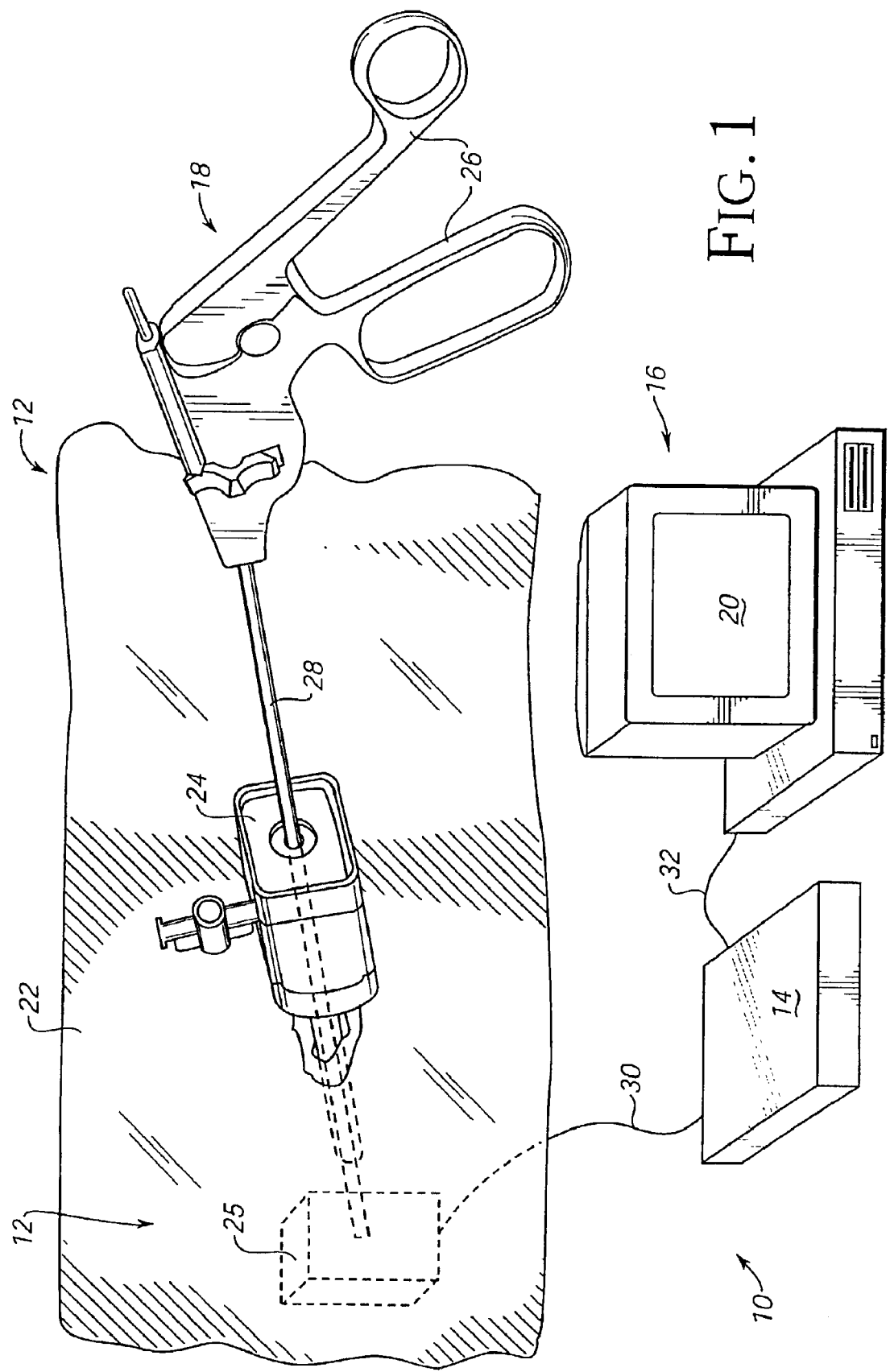
FIG. 1 is a schematic illustration of the present invention being used for medical simulation purposes.

FIG. 1 illustrates an example of the use of the present invention for medical simulation purposes. A virtual reality system 10 used to simulate a medical procedure includes a human/computer interface apparatus 12, an electronic interface 14, and a host computer 16. The illustrated virtual reality system 10 is directed to a virtual reality simulation of a laparoscopic surgery procedure.

The handle 26 of a laparoscopic tool 18 used in conjunction with the present invention is manipulated by an operator and virtual reality images are displayed on a display device 20 of A digital processing system in response to such manipulations. For example, when the tool 18 is moved by the user, a graphical representation of the tool or a part of the tool may be moved correspondingly within a graphical environment displayed on device 20. Display device 20 may be a standard display screen or CRT, 3-D goggles, or any other visual interface. The digital processing system is typically a host computer 16. The host computer can be a personal computer or workstation or other computer device or processor, such as a home video game system commonly connected to a television set, such as systems available from Nintendo, Sega, or Sony; a "set top box" which may be used, for example, to provide interactive television functions to users; an arcade game; a portable computing device, etc. Multiple tools 18, each manipulatable by the user, may also be provided, as in a preferred embodiment described below.

Host computer 16 implements a host application program with which a user is interacting via peripherals and interface device 14. For example, the host application program may be a video game, medical simulation, scientific analysis program, or even an operating system or other application program that utilizes force feedback. Typically, the host application provides images to be displayed on a display output device, as described below, and/or other feedback, such as auditory signals. The medical simulation example of FIG. 1 includes a host medical simulation application program. Suitable software for such applications is available from Immersion Corporation of San Jose, Calif. Alternatively, display screen 20 may display images from a game application program or other program.

One example of a human/interface apparatus 12 as illustrated herein is used to simulate a laparoscopic medical procedure. In addition to the handle of a standard laparoscopic tool 18, the human/interface apparatus 12 may include a barrier 22 and a standard laparoscopic trocar 24 (or a facsimile of a trocar). The barrier 22 is used to represent a portion of the skin covering the body of a patient. Trocar 24 is inserted into the body of the virtual patient to provide an entry and removal point from the body of the patient for the laparoscopic tool 18, and to allow the manipulation of the laparoscopic tool. Barrier 22 and trocar 24 may be omitted from apparatus 12 in other embodiments if desired. Preferably, the laparoscopic tool 18 is modified; in one embodiment, the shaft is replaced by a linear axis member, as described below. In other embodiments, the end of the shaft of the tool (such as any cutting edges) may be removed. The distal end of the laparoscopic tool 18 may not be required for the virtual reality simulation.

The laparoscopic tool 18 includes a handle or "grip" portion 26 and a shaft portion 28. The shaft portion is an elongated mechanical object, described in greater detail below. In one embodiment, the present invention is concerned with tracking the movement of the shaft portion 28 in three-dimensional space, e.g. four degrees of freedom. The shaft 28 is constrained at some point along its length such that it may move with four degrees of freedom within the simulated patient's body.

A mechanical apparatus 25 for interfacing mechanical input and output is shown within the "body" of the patient in phantom lines. When an interaction is simulated on the computer, the computer will send feedback signals to the tool 18 and mechanical apparatus 25, which has actuators for generating forces in response to the position of the virtual laparoscopic tool relative to surfaces or features displayed on the computer display device. Mechanical apparatus 25 is described in greater detail below. Signals may be sent to and from apparatus 25 via interface 30, which may be similar to interface 72 described below.

While one embodiment of the present invention will be discussed with reference to the laparoscopic tool 18, it will be appreciated that a great number of other types of objects may be used with the method and apparatus of the present invention. In fact, the present invention may be used with any mechanical object where it is desirable to provide a human/computer interface with one to six degrees of freedom. Such objects may include endoscopic or other similar surgical tools used in medical procedures, catheters, hypodermic needles, wires, fiber optic bundles, styluses, joysticks, screw drivers, pool cues, hand grips, etc.

The electronic interface 14 is a component of the human/computer interface apparatus 12 and may couple the apparatus 12 to the host computer 16. Electronic interface 14 may be included within a housing of mechanical apparatus 25, within host computer 16, or may be provided as a separate unit. More particularly, interface 14 is used in preferred embodiments to couple the various actuators and sensors of apparatus 25 (described in detail below) to computer 16. In some embodiments, the interface may include a microprocessor local to the apparatus 25 to handle sensor data and actuator control. Suitable electronic configurations are described, for example, in U.S. Pat. Nos. 5,623,582; 5,821, 920; 5,731,804; 5,734,373; 5,828,197; and 6,024,576, all of which are incorporated herein by reference.

Signals may be sent to and from interface 14 and computer 16 by a standard interface 32 (RS-232, USB, Firewire, serial, parallel, etc.) or by wireless transmission and reception. In various embodiments of the present invention, interface 14 may serve solely as an input device for the computer 16, solely as an output device for the computer 16, or as an input/output (I/O) device for the computer 16. The interface 14 may also receive inputs from other input devices or controls that are associated with apparatus 12 and may relay those inputs to computer 16. For example, commands sent by the user activating a button on apparatus 12 may be relayed to computer 16 to implement a command or cause the computer 16 to output a command to the apparatus 12.

Figure 2A:
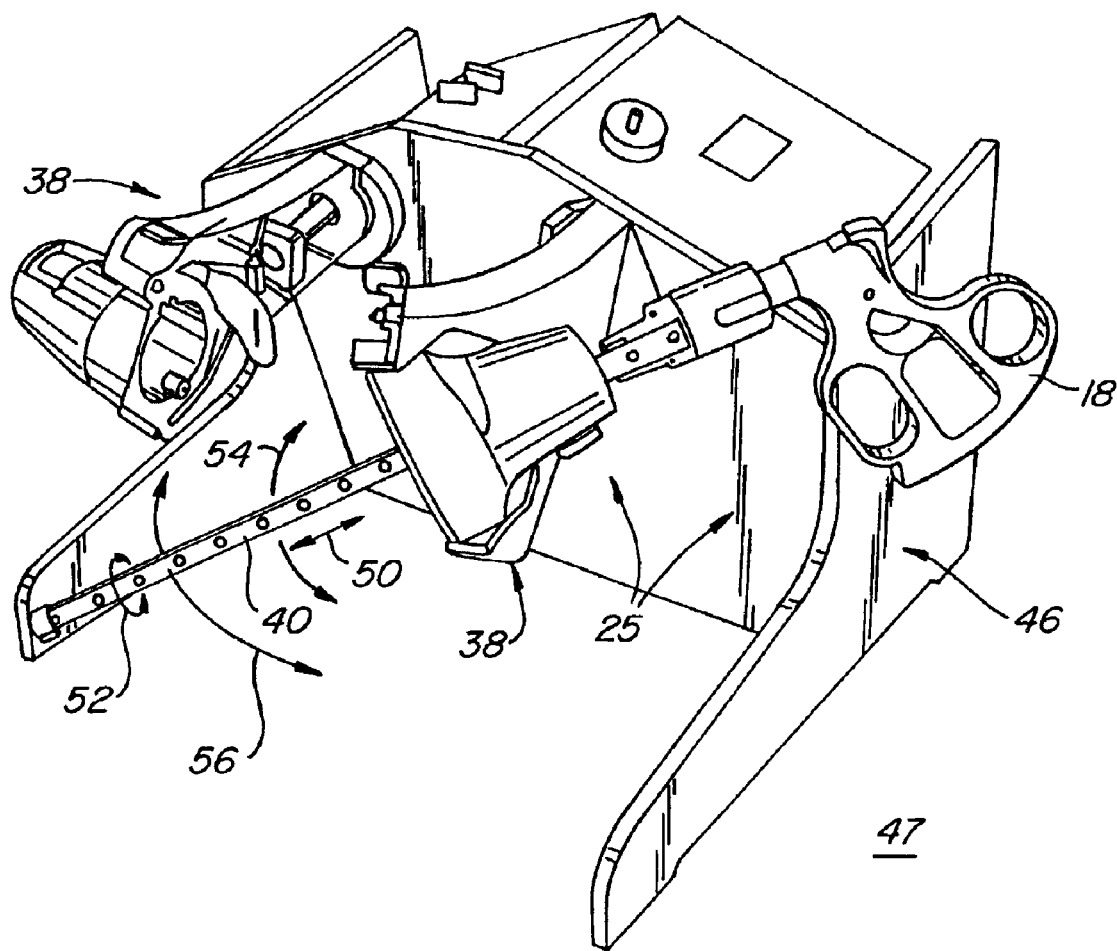
FIGS. 2A and 2B are perspective view of a mechanical simulation apparatus in accordance with the present invention.
Figure 2B:
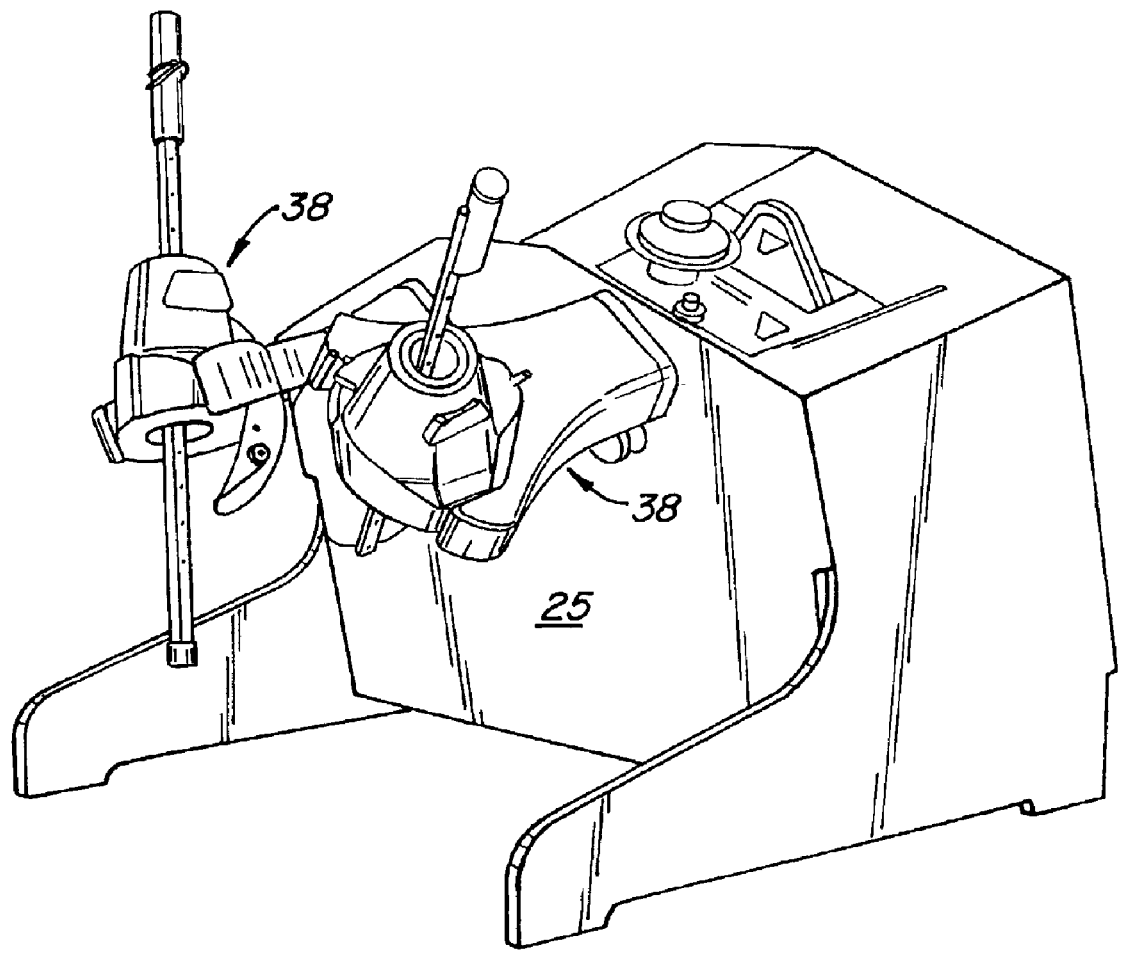

In FIGS. 2A and 2B, perspective views of mechanical apparatus 25 for providing mechanical input and output in accordance with the present invention are shown. Apparatus 25 may include two or more tools 18 (only one is shown) to allow a user to realistically simulate an actual surgical procedure using laparoscopic instruments. A user may manipulate each of the tools 18 independently, where each tool is independently sensed and actuated in the present invention.

Each tool 18 is coupled to a linear axis member 40, which is coupled to a mechanical linkage 38, which will be described in more detail below. The user object 44, such as a handle, is preferably coupled to linear axis member 40. The mechanical linkage is grounded via a base structure 46. The actuators, such as DC motors, which output the forces on each linear axis member 40 and tool 18, are in the described embodiment located within the base structure 46, and are therefore all grounded. This configuration allows high fidelity and efficient haptic feedback to be produced with the apparatus 25. The actuators may also include sensors which sense the rotation of the actuators and thus, detect the motion of the tool in the four degrees of freedom. In other embodiments, sensors may be coupled to parts of the linkage 38 to sense the motion of the tool more directly.

In the described embodiment, each linear axis member 40/tool 18 may be moved in four degrees of freedom, shown as the insert degree of freedom 50, the twist degree of freedom 52, the first rotation (yaw) 54, and the second rotation (pitch) 56. Other embodiments may limit the degrees of freedom to a lesser number, or provide additional degrees of freedom.

Figure 2C:
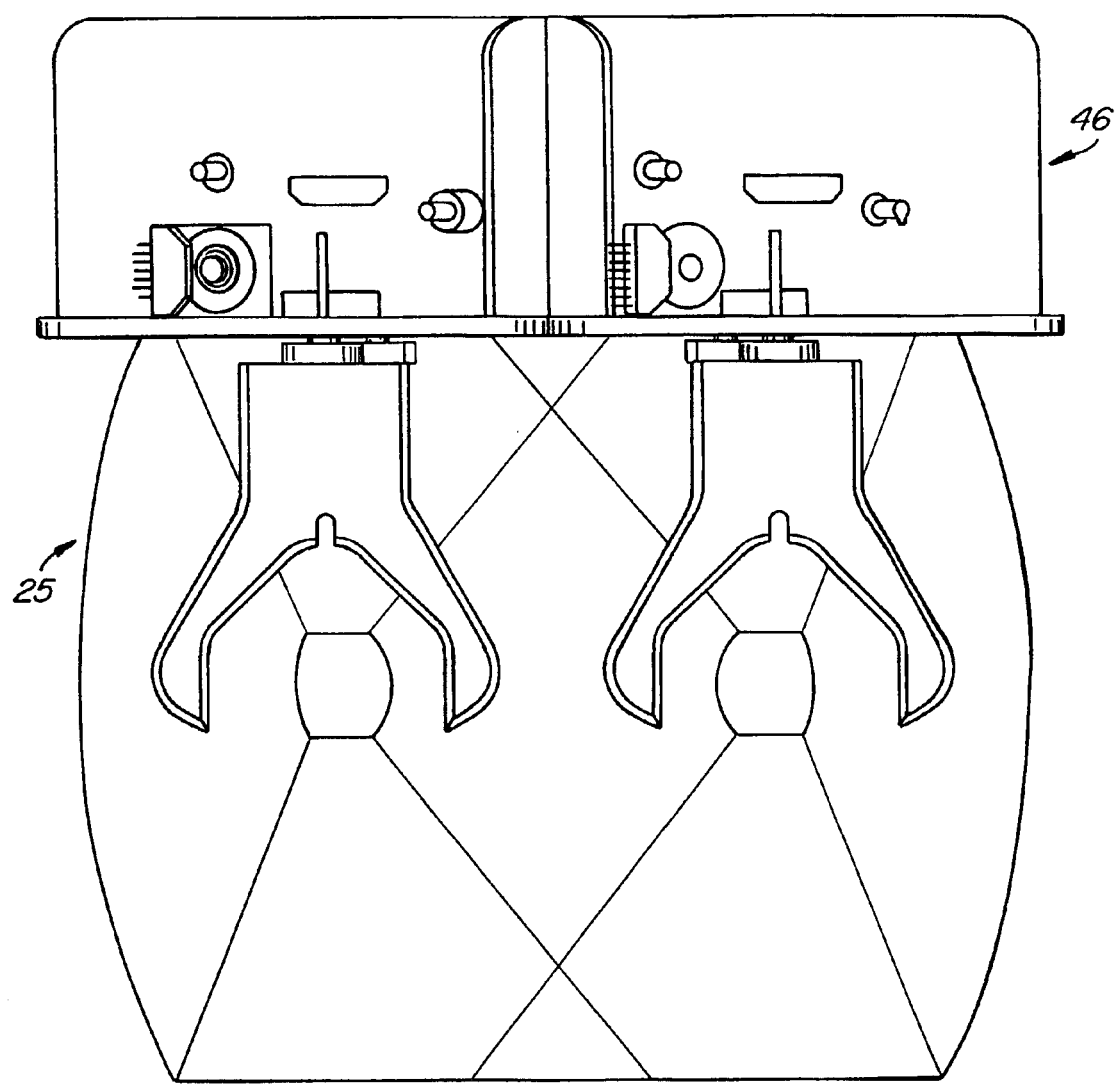
FIGS. 2C and 2D are elevational views of the base structure and portions of the linkage mechanisms of the mechanical simulation apparatus.
Figure 2D:
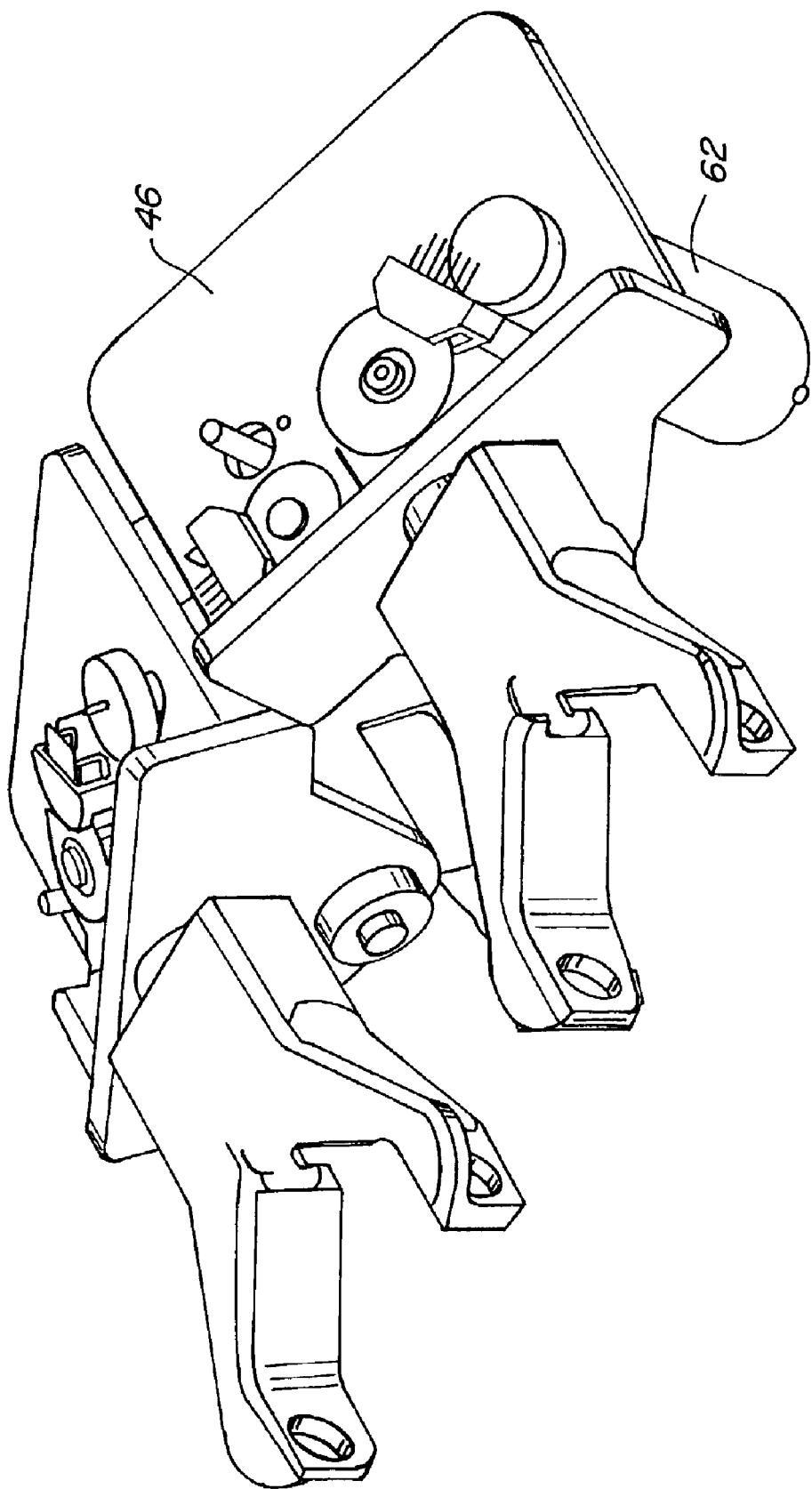

FIGS. 2C and 2D further illustrate the base structure 46 and portions of the linkage mechanisms 38 that are rotatably coupled to the base structure.

Figure 2E:
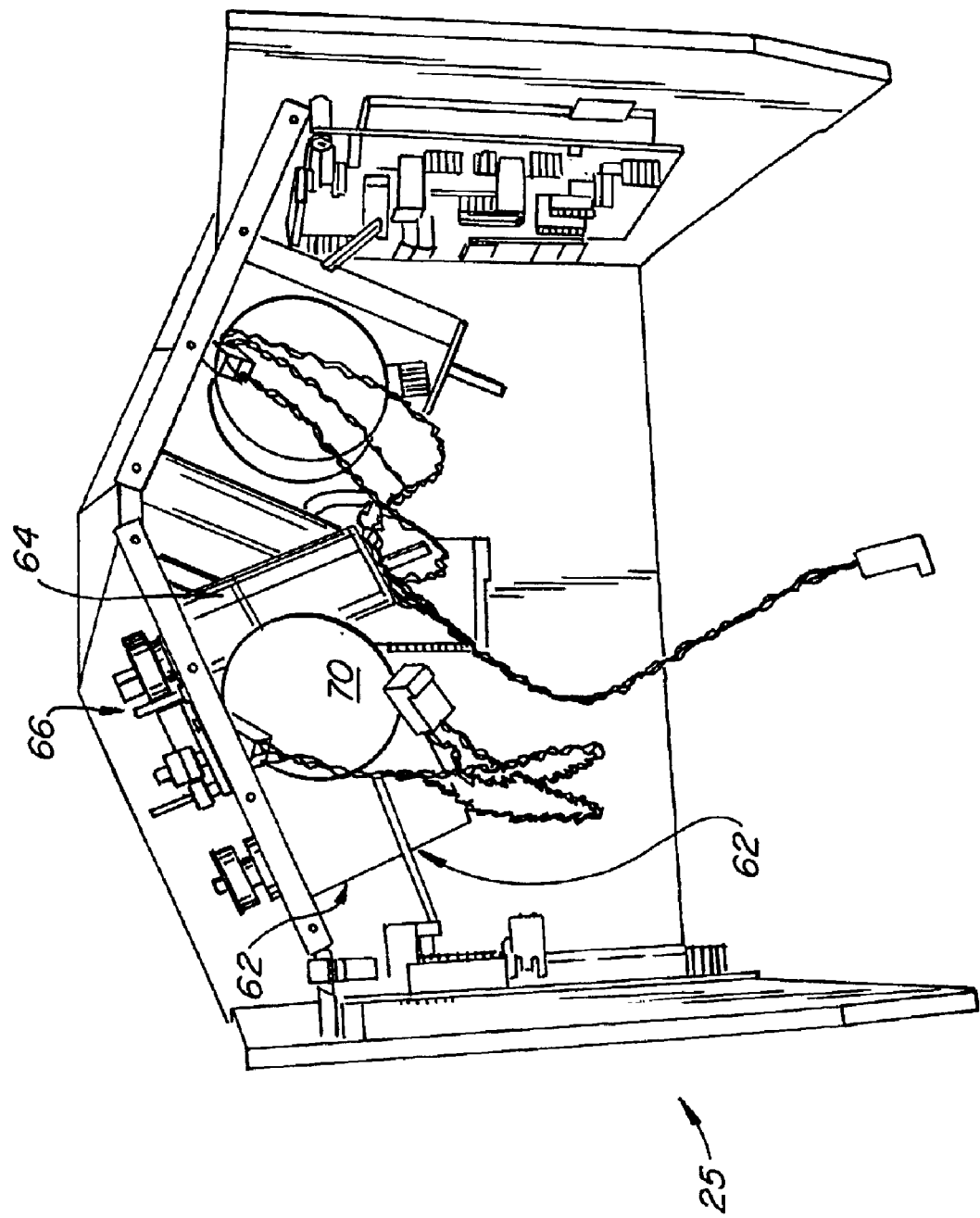
FIG. 2E is a rear view of the mechanical simulation of the apparatus in accordance with the present invention.

FIG. 2E illustrates a rear view of the apparatus 25 showing many of the actuators and some of the sensors of the described embodiment. A rotary actuator 62, such as a DC motor, drives the insert degree of freedom 50, a rotary actuator 64 drives the yaw degree of freedom 54, and a rotary actuator 66, positioned behind actuator 64 in FIG. 2E, drives the twist degree of freedom 52. An actuator-sensor pair 70 drives the pitch degree of freedom 56.

Figure 2F:
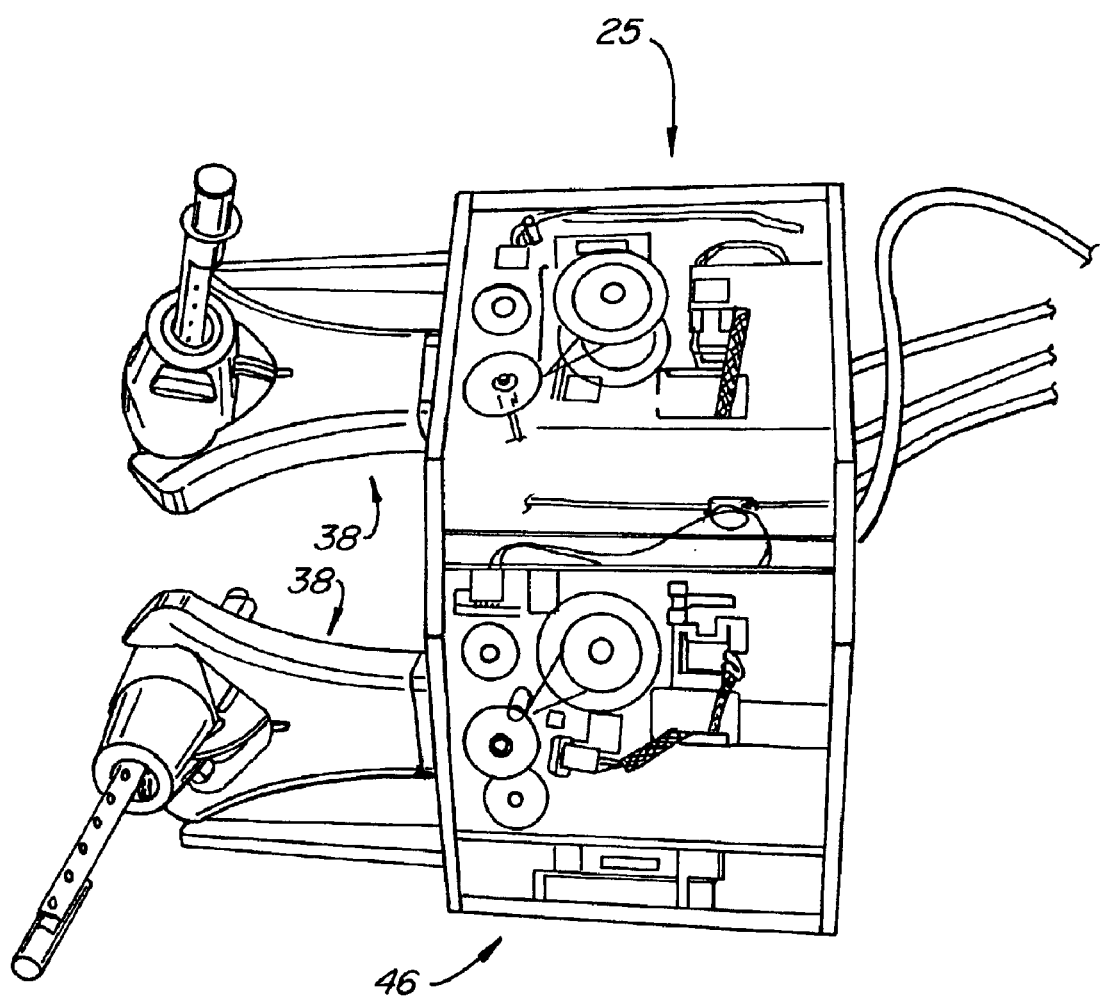
FIG. 2F is a top view of the mechanical simulation apparatus in accordance with the present invention.
Figure 2G:
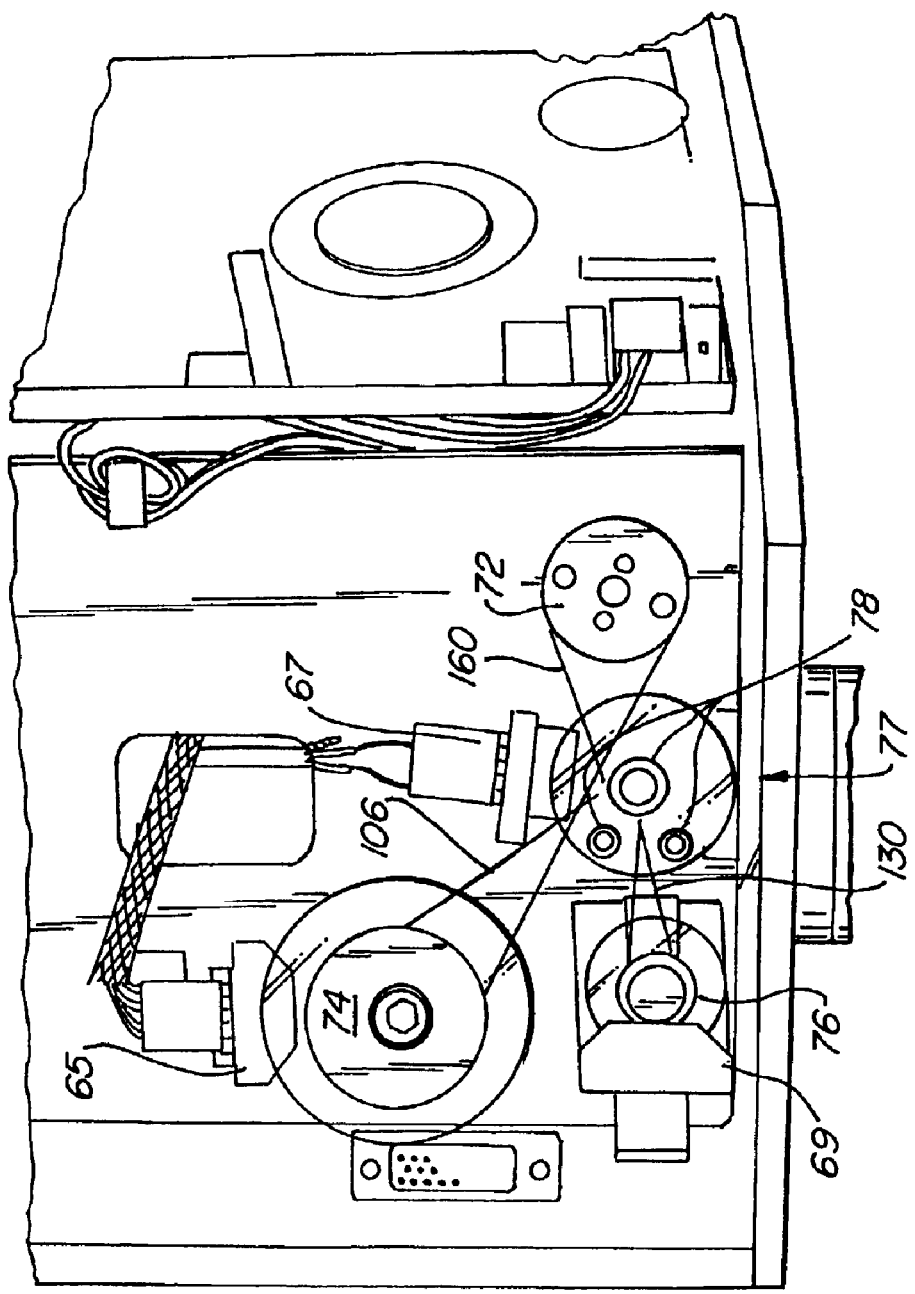
FIG. 2G is a close up of top surfaces of the mechanical simulation apparatus in accordance with the present invention.

FIG. 2F illustrates a top view of the apparatus 25 and FIG. 2g is a close up of the top surfaces of the apparatus. A pulley 72 is coupled to actuator 62 and has a cable 160 wrapped around it. A pulley 74 is coupled to the actuator 64 and has a cable 106 wrapped around it. A pulley 76 is coupled to the actuator 66 and has a cable 130 wrapped around it. These cables are described in greater detail below. The cables are all routed to the mechanical linkage 38 through an aperture 77 in the side of the base structure; in the described embodiment, the cables may each be wrapped around its own central spindle 78 before being routed to their respective pulleys 72, 74, or 76. In the described embodiment, a sensor 65 senses the motion of the shaft of actuator 64, a sensor 67 senses the motion of the spindle 78 connected to the shaft of actuator 62, and a sensor 69 senses the motion of the shaft of actuator 66. The sensors are optical encoders having emitters and detectors sensing marks on an encoder wheel coupled to the pulley or spindle, as shown. In the described embodiment, the sensor for the pitch degree of freedom 56 is provided on the housing of actuator/sensor 70 to measure the actuator shaft rotation directly.

Other types of sensors and actuators, which essentially serve as transducers for the system, may be used in other embodiments, such as analog potentiometers, Polhemus (magnetic) sensors, lateral effect photo diodes, etc. Alternatively, sensors may be positioned at other locations of relative motion or joints of mechanical apparatus 25. It should be noted that the present invention may utilize both absolute and relative sensors. The actuators may also be of various types, such as active actuators and/or passive actuators. Active actuators may include linear current control motors, stepper motors, pneumatic/hydraulic active actuators, stepper motor, brushless DC motors, pneumatic/ hydraulic actuators, a torquer (motor with limited angular range), a voice coil, and other types of actuators that transmit a force to move an object. Passive actuators may also be used. Magnetic particle brakes, friction brakes, or pneumatic/hydraulic passive actuators may be used in addition to or instead of a motor to generate a damping resistance or friction in a degree of motion. In addition, in some embodiments, passive (or "viscous") damper elements may be provided on the bearings of apparatus 25 to remove energy from the system and intentionally increase the dynamic stability of the mechanical system. In other embodiments, this passive damping may be introduced by using the back electromotive force (EMF) of the actuators to remove energy from the system. In addition, in the voice coil embodiments, multiple wire coils may be provided, where some of the coils may be used to provide back EMF and damping forces.

The actuators and sensors are decoupled, meaning that these transducers are directly coupled to ground member 46 which is coupled to a ground surface 47, i.e. the ground surface carries the weight of the transducers, not the user handling tool 18. The weights and inertia of the transducers are thus substantially negligible to a user handling and moving the tool. This provides a more realistic interface to a virtual reality system, since the computer may control the transducers to provide substantially all of the forces felt by the user in these degrees of motion. In contrast, in typical prior art arrangements of multi-degree of freedom interfaces, one actuator "rides" upon another actuator in a serial chain of links and actuators. This low bandwidth arrangement causes the user to feel the inertia of coupled actuators when manipulating an object.

Optionally, additional transducers may be added to apparatus 25 to provide additional degrees of freedom for the tool 18. For example, a transducer may be added to the grip of laparoscopic tool 18 to sense and/or output forces to the degree of freedom provided by the user moving two portions of a tool 18 relative to each other to simulate extending the cutting blade of the tool, for example.

Figure 3B:
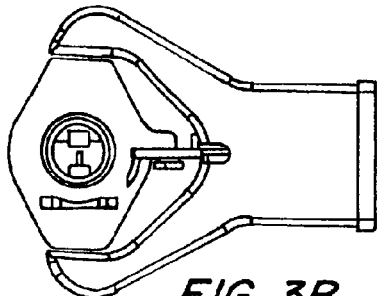
FIG. 3B is a top view of the mechanical linkage.
Figure 3A:
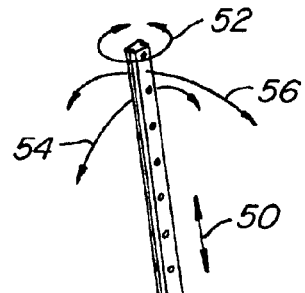
FIG. 3A is a perspective view of a mechanical linkage of the mechanical simulation of the apparatus in accordance with the present invention.
Figure 3C:
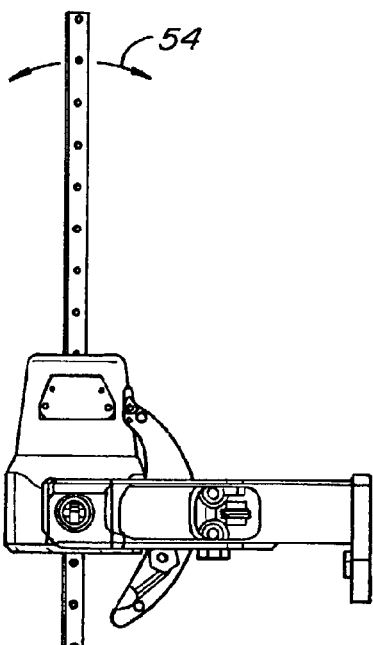
FIG. 3C is a side view of the mechanical linkage.
Figure 3D:
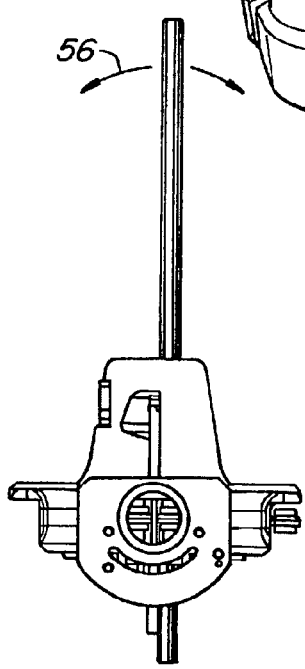
FIG. 3D is a front view of the mechanical linkage.
Figure 3E:
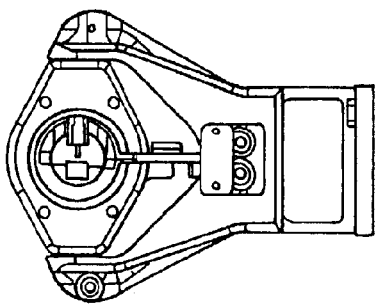
FIG. 3E is a bottom view of the mechanical linkage.

FIGS. 3A (perspective view), 3B (top view), 3C (side view), 3D (front view), and 3E (bottom view) illustrate the mechanical linkage 38 of the apparatus 25. The linkage 38 is rotatably coupled to the base structure 46 to allow the second rotation 56, where cables from various moving parts of the linkage 38 extend to the actuators of the base structure, as detailed below. Linear axis member 40 may be moved relative to the linkage 38 to provide two degrees of freedom 50 and 52, and moves with portions of the linkage to provide two other degrees of freedom 54 and 56.

Figure 4A:
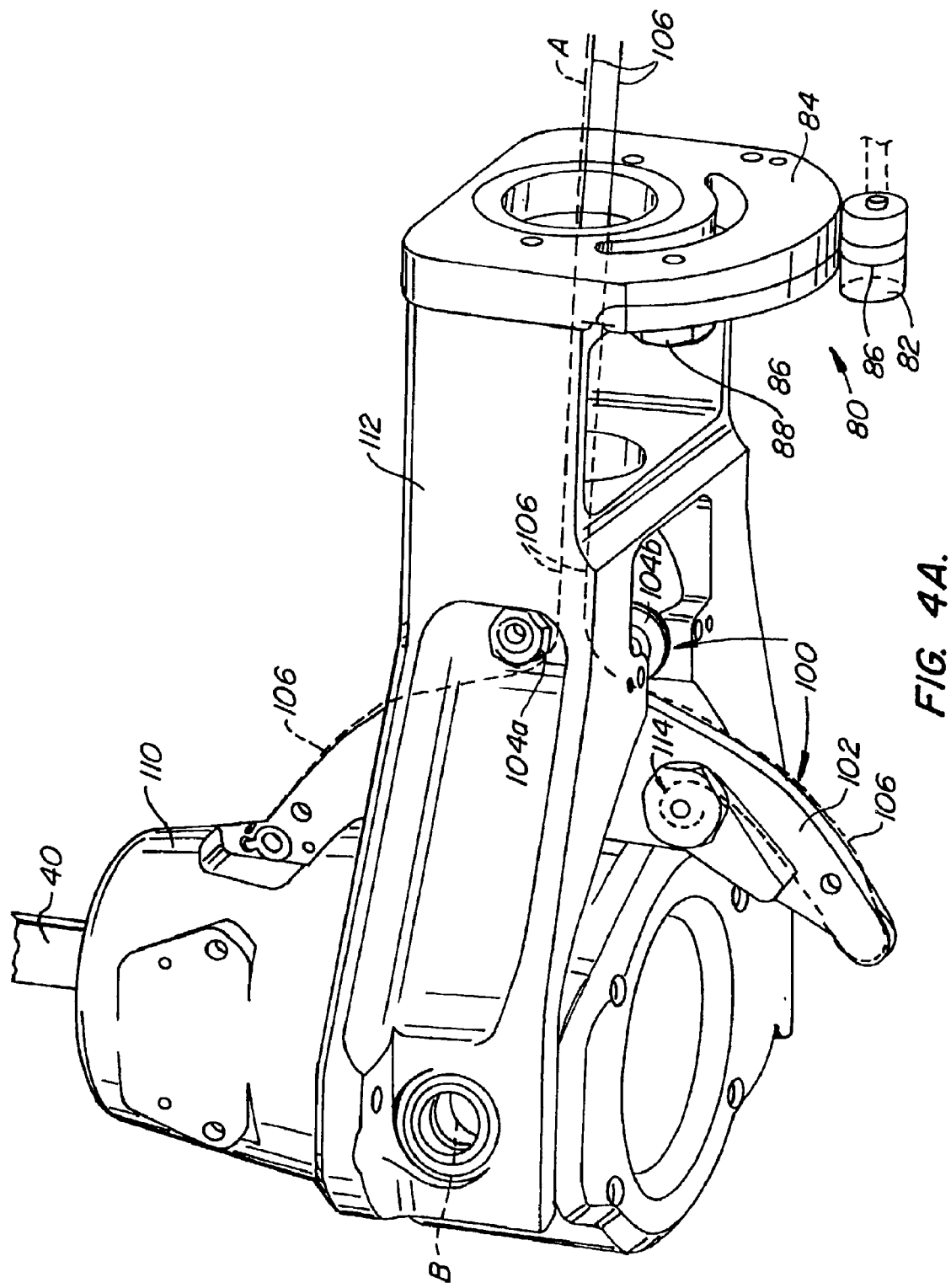
FIGS. 4A and 4B are perspective views of the mechanical linkage.
Figure 4B:
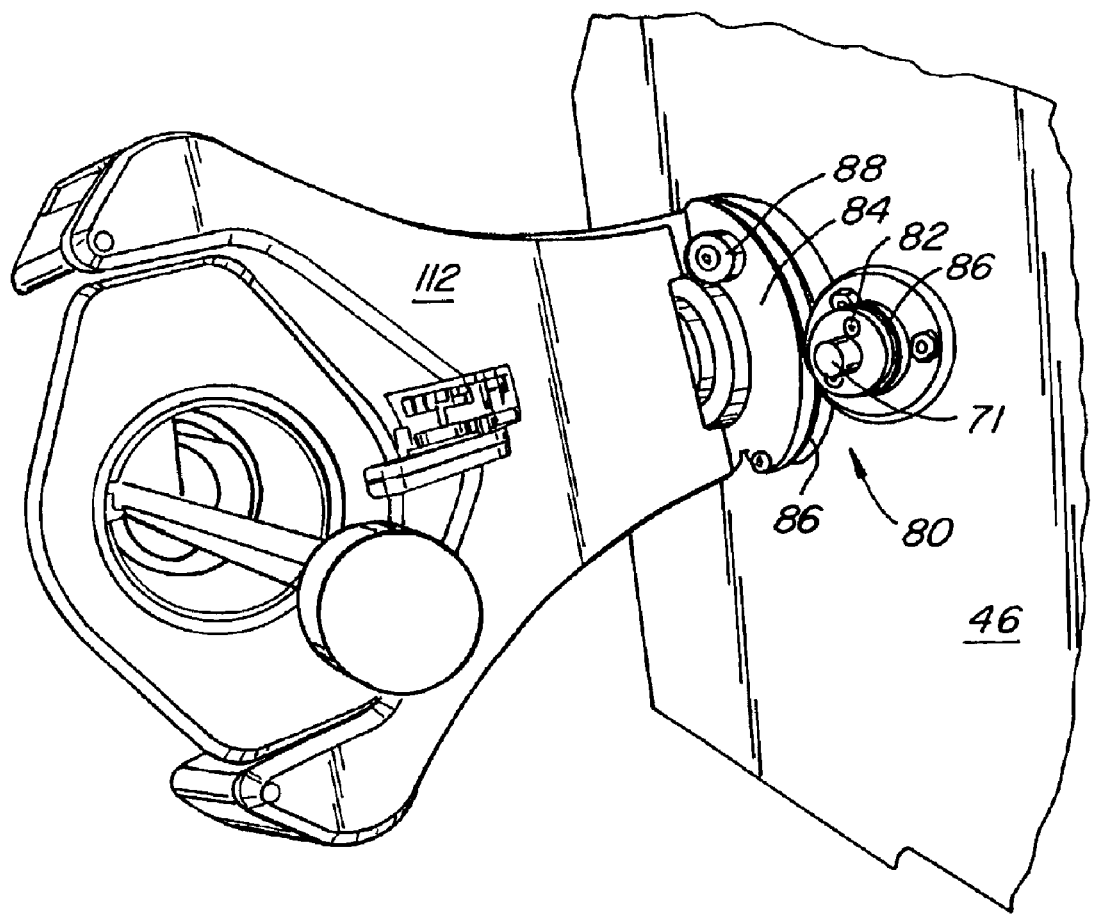

FIGS. 4A and 4B shows a perspective view of mechanical linkage 38. The second rotation (pitch) 56 is provided by a mechanical bearing positioned between the linkage 38 and the base structure 46. To provide forces in the second rotation 56 from grounded actuator 70, a capstan drive 80 may be a mechanical transmission transmitting forces from the actuator to the linkage 38. A capstan pulley 82 may be rigidly coupled to the rotating shaft 71 of the actuator 70, where the pulley has an axis of rotation parallel to the axis of rotation A of the linkage 38 for the degree of freedom 56 and the pulley is positioned adjacent to a drum 84 that is rigidly coupled to the linkage 38 as shown. A cable 86 is connected at one end of the drum 84, routed along the edge of the drum, around the pulley 82 one or more times, and is routed along the remaining edge of the drum to its other side. The cable may be tensioned using tensioning nut 88, for example. Other types of transmissions may be used in other embodiments, e.g. gears, friction wheels, belt drives, etc.

The first rotation (yaw) 54 of linkage 38 is provided by a different cable drive 100. Cable drive 100 includes a drum 102 which is rigidly coupled to linkage member 110, which rotates about degree of freedom 54 about axis B with respect to linkage member 112. Two idler pulleys 104a and 104b are rotatably coupled to linkage member 112 and rotating about axes parallel to axis B. A cable 106, shown as a dashed line, is routed from one end of drum 102, around idler pulley 104a, through the linkage member 38 and out to the base structure and driven pulley 74 of actuator 64, where it is wrapped multiple times. The cable then is routed back into and through the linkage 38, around the idler pulley 104b, and along the edge of drum 102 to the tensioner 114. This configuration allows the actuator to rotate the linkage member 110 by pulling the desired side of the drum 102 with the cable 106.

Figure 5A:
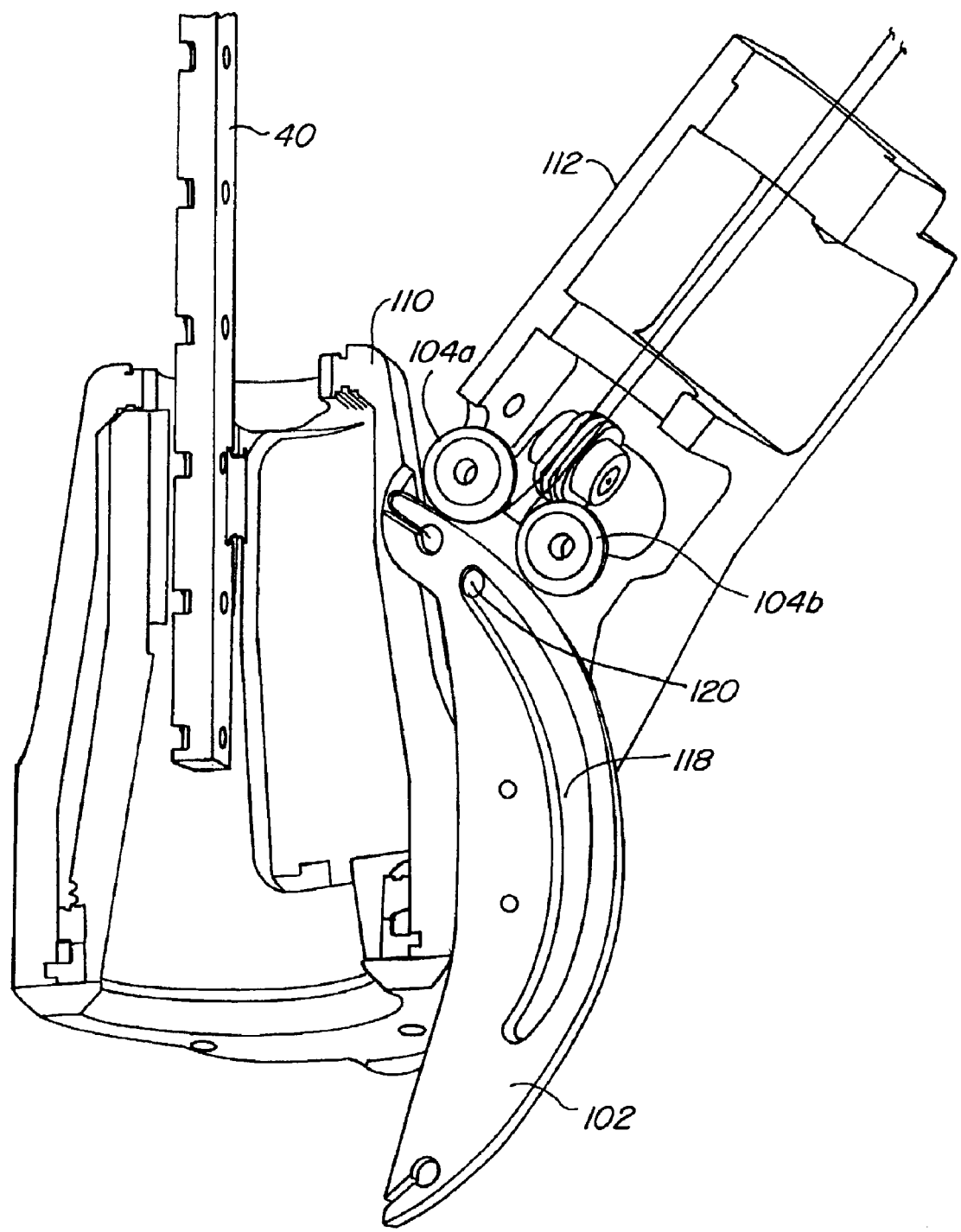
Figure 5C:
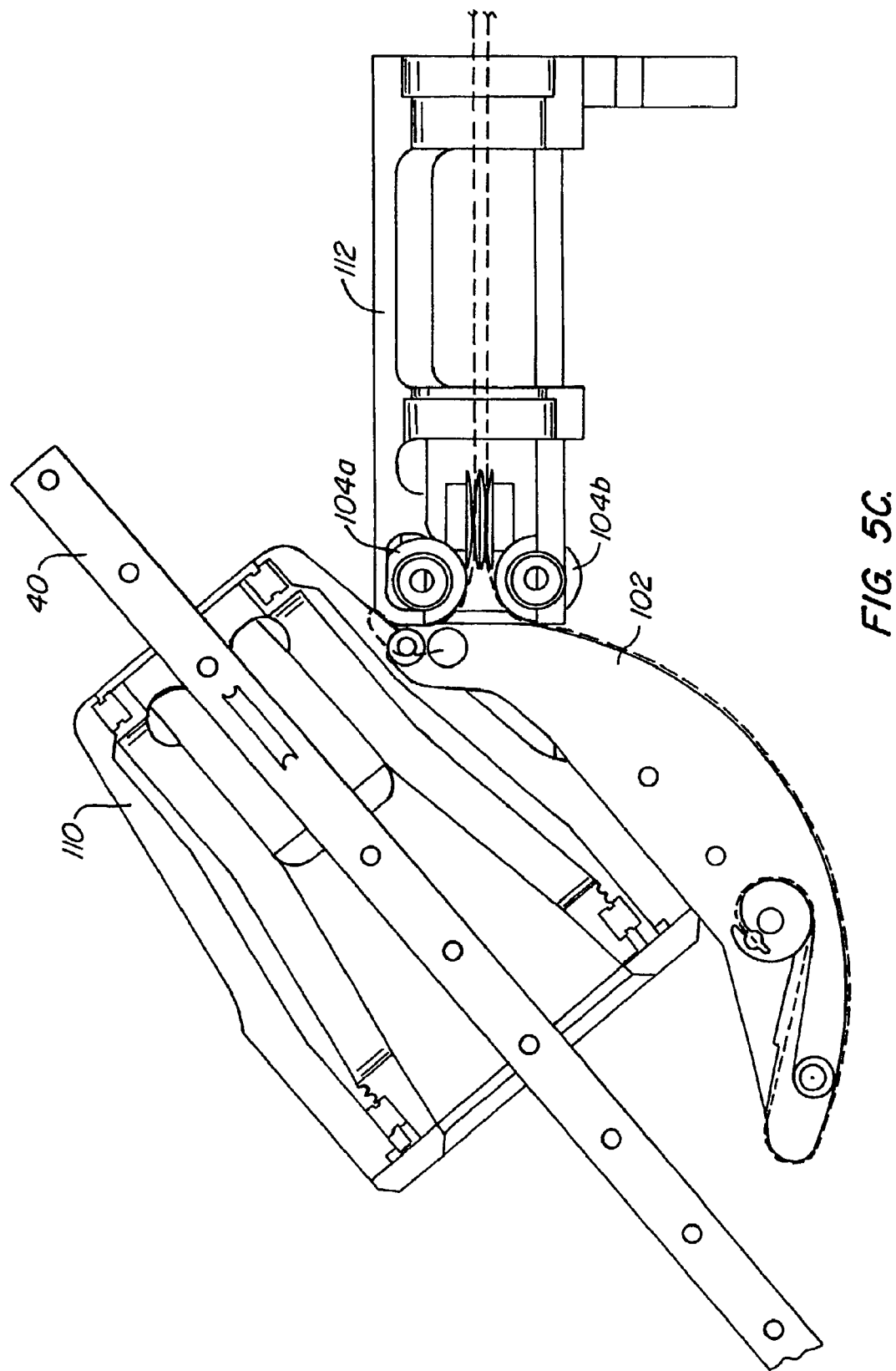
Figure 5D:
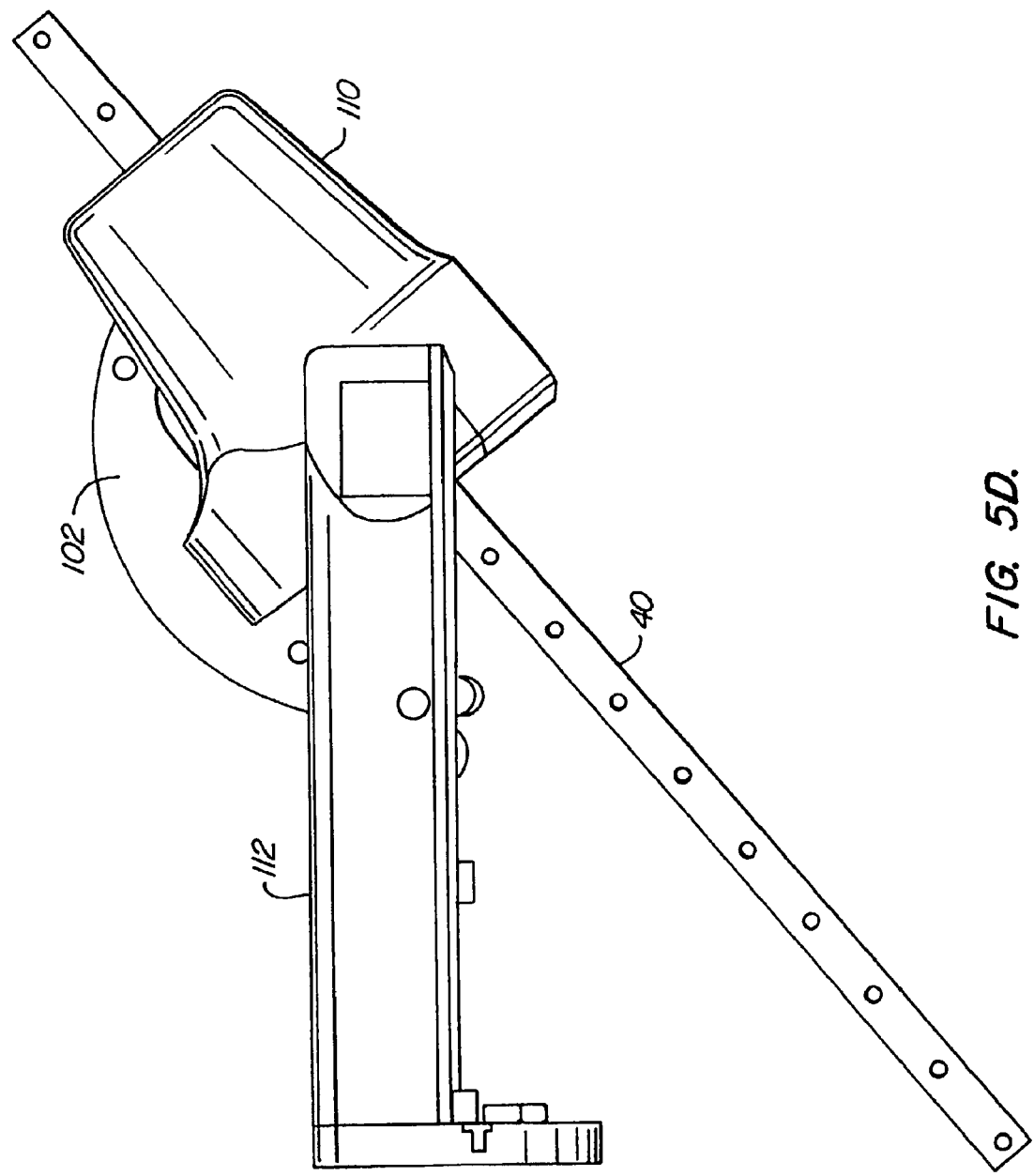

FIGS. 5A, 5B, 5C, and 5D are other side sectional views of the linkage 38, where examples of extremes of rotation of the linkage member 110 with respect to the linkage member 112 are shown. The motion may be limited by stops provided in the path of movement of the drum 102. For example, as shown in FIG. 5A, an opening 118 may be placed in the drum 102. A stop member 120, such as a cylinder, may be coupled to the linkage member 112 and positioned within the opening 118, so that the stop member 120 will engage the ends of the opening 118 to provide the limits of motion of the drum.

Figure 6A:
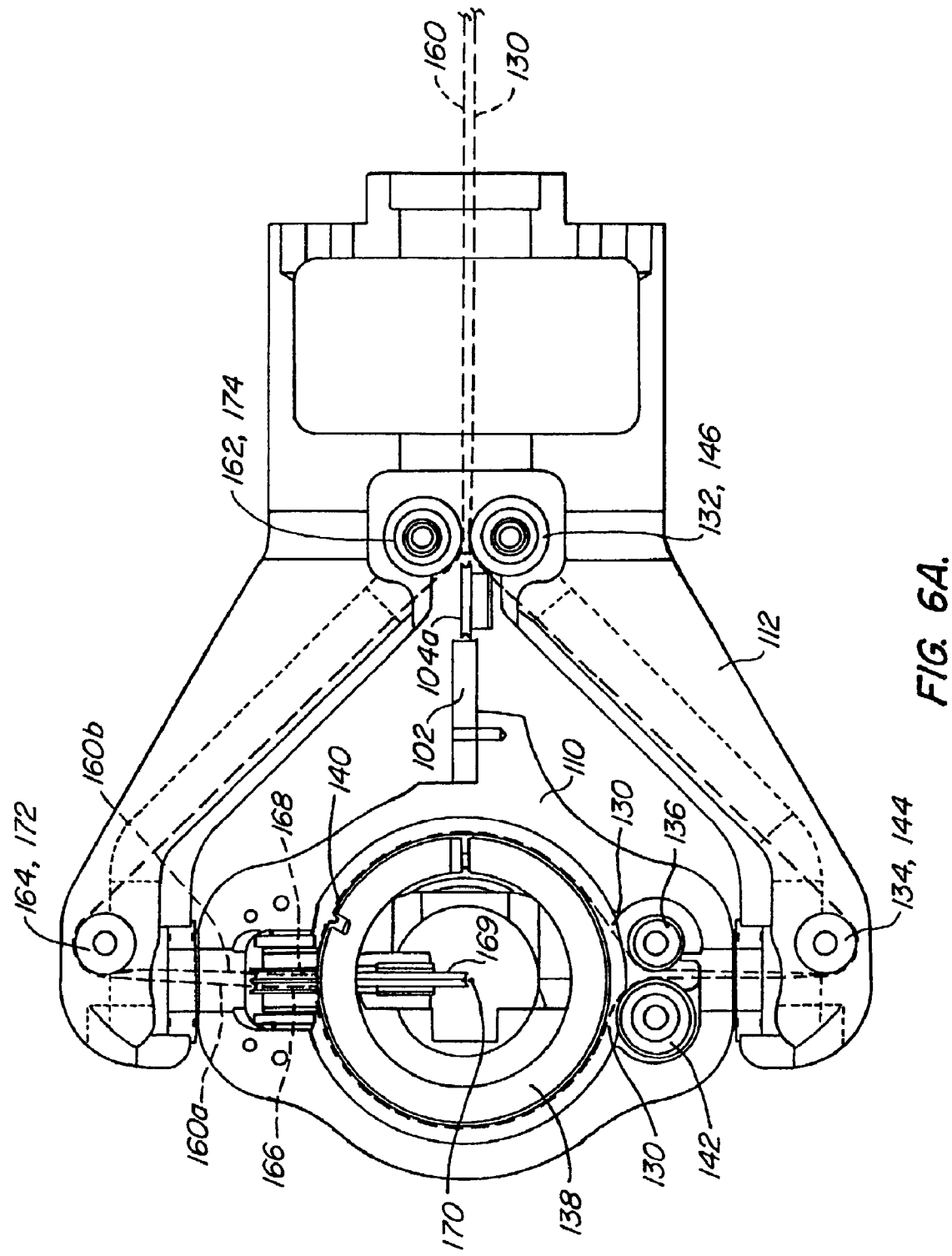
FIGS. 6A and 6B are bottom and perspective bottom views, respectively, of the mechanical linkage.
Figure 6B:
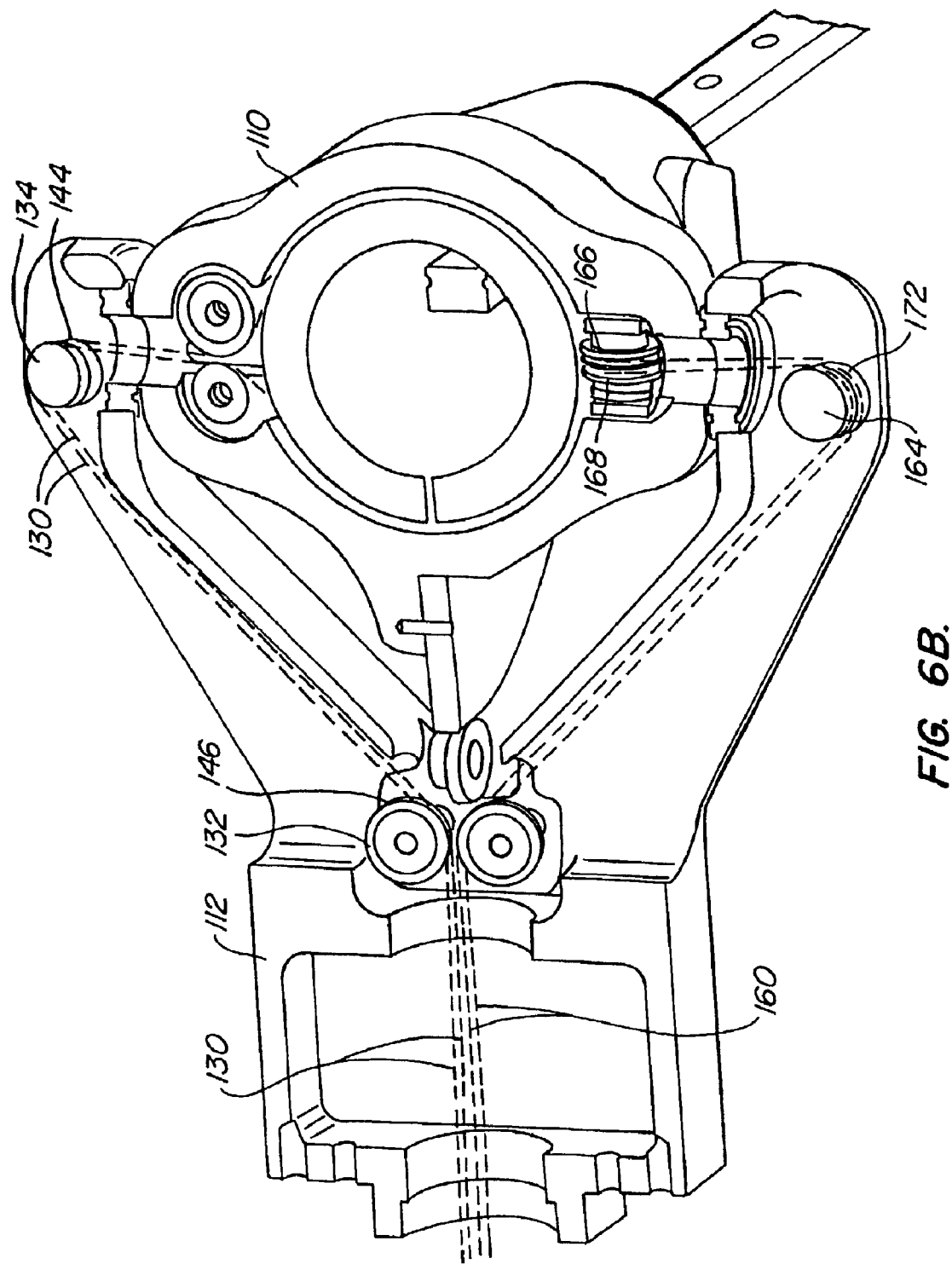

FIGS. 6A and 6B are bottom and perspective bottom views, respectively, of the linkage mechanism 38. To allow forces to be output in the twist degree of freedom 52, a first end of cable 130 (represented by a dashed line) is routed from directly-driven pulley 76 of the actuator 66 in the base structure 46 and through the linkage mechanism 38. The cable 130 is routed around an idler pulley 132, around another idler pulley 134, and around another idler pulley 136. The cable 130 is then wrapped counterclockwise (as viewed in FIG. 6a) around a rotatable drum 138 and connected to the drum at a point 140 (point 140 may be located elsewhere in other embodiments). The other, second end of the cable 130 is also connected to the drum 138 at point 140 and may be wrapped counterclockwise (as viewed in FIG. 6a) on the remaining side around the drum 138 to the pulley 142. Cable 130 is routed from the second end around idler pulley 142 and then idler pulley 144, where idler pulley 144 and idler pulley 134 are positioned adjacent to each other and have the same axis of rotation. Cable 130 is then routed around idler pulley 146, which is positioned adjacent to and has the same axis of rotation as pulley 132. The cable 130 is then routed through the linkage member 38, both ends represented by line 130, to the actuator 66 in the base structure, where it is wrapped multiple times around the pulley 76 directly driven by the actuator 66.

In operation, the actuator 66 may rotate the drum 138 in either direction, thereby rotating the linear axis member 40 and tool 18. When the actuator shaft is rotated in one direction, the first end of cable 130 around pulley 136 is pulled, causing the drum to rotate about center point 170 in the corresponding direction. When the actuator shaft is rotated in the opposite direction, the second end of cable 130 is pulled around pulley 142, causing the drum to rotate about central point 170 in its other direction.

To allow forces to be output in the linear insert degree of freedom 50, a first end of cable 160 (represented by dashed line in FIG. 6a) is routed from directly-driven pulley 72 of actuator 62 in the base structure 46 through the linkage mechanism 38. The cable 160 is routed around idler pulley 162, around idler pulley 164, and then around idler pulley

166. This first end 161 of cable 160 is then routed around pulley 169 (shown in FIG. 7*a*) and is coupled to the linear axis member 40. The second end 162 of the cable 160 is coupled to the linear axis member 40 on the other side of the central pivot point 170. The cable 160 is routed from the second end, around pulley 168, around pulley 172 which is adjacent to and rotates about the same axis as pulley 164, and around pulley 174 which is adjacent to and rotates about the same axis as pulley 162. The cable is then routed through the linkage mechanism 38 to the pulley 72 driven by the actuator 62, where it is wrapped multiple times.

In operation, the actuator 62 may rotate its driven pulley in either direction to correspondingly pull on the first end or the second end of the cable 160. If the first end is pulled, a downward force on the linear axis member 40 (as oriented in FIG. 3) is output, while if the second end is pulled, an upward force on the linear axis member is output.

Figure 7A:
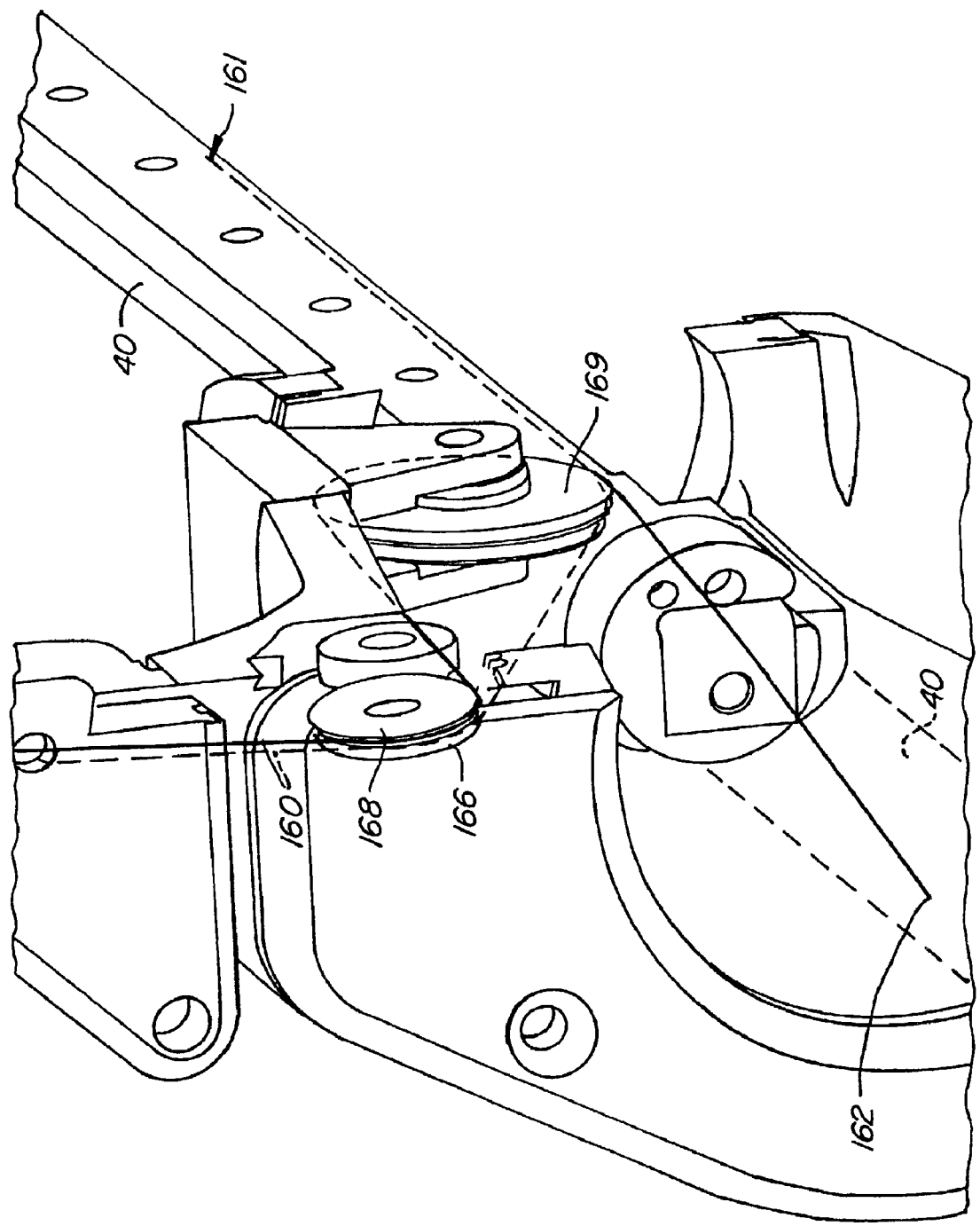
Figure 7B:
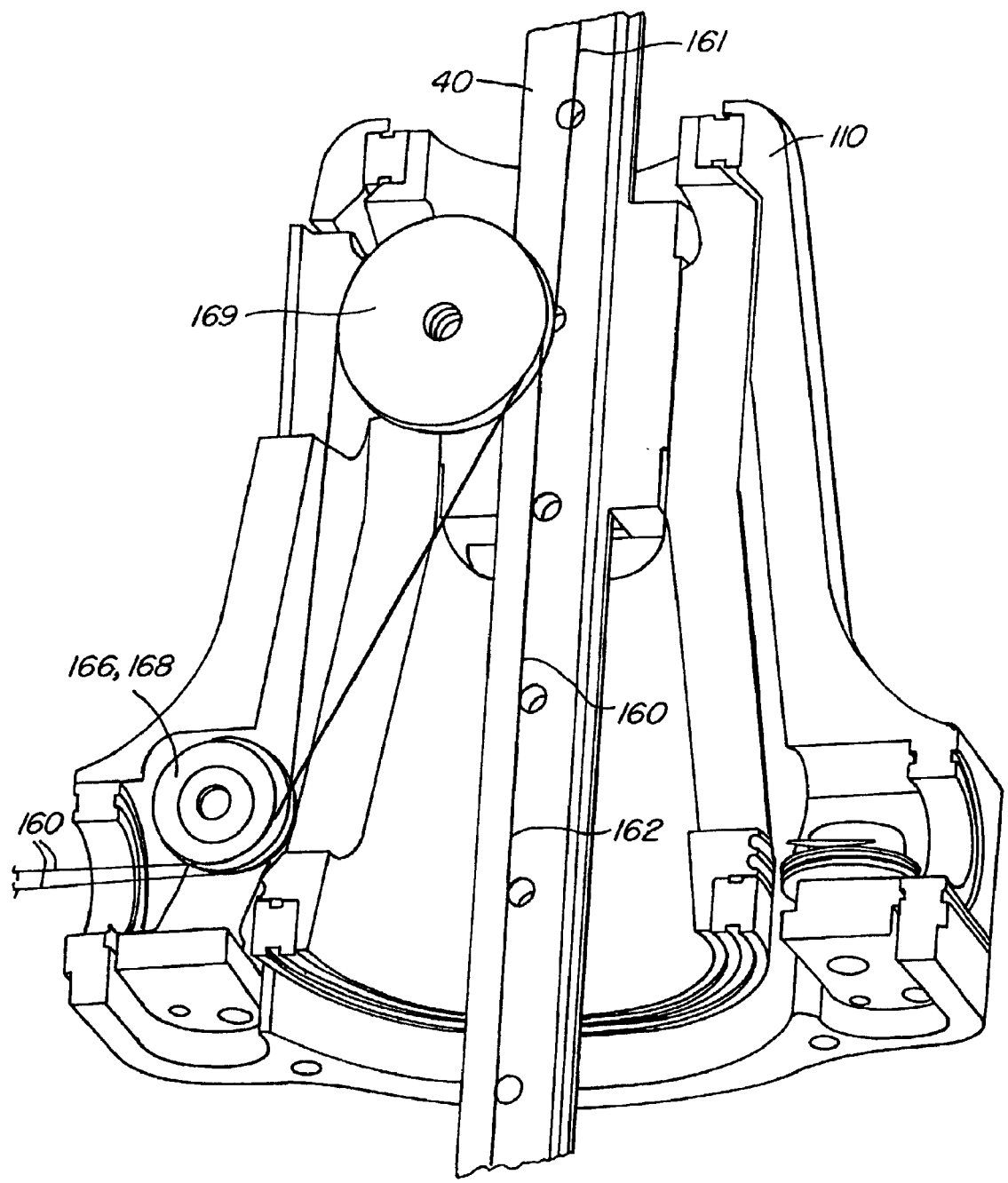

FIGS. 7A–7C are additional sectional perspective views of the linkage mechanism 38 and the cables and pulleys described above, illustrating the mechanism of the insert degree of freedom 50.

Figure 8A:
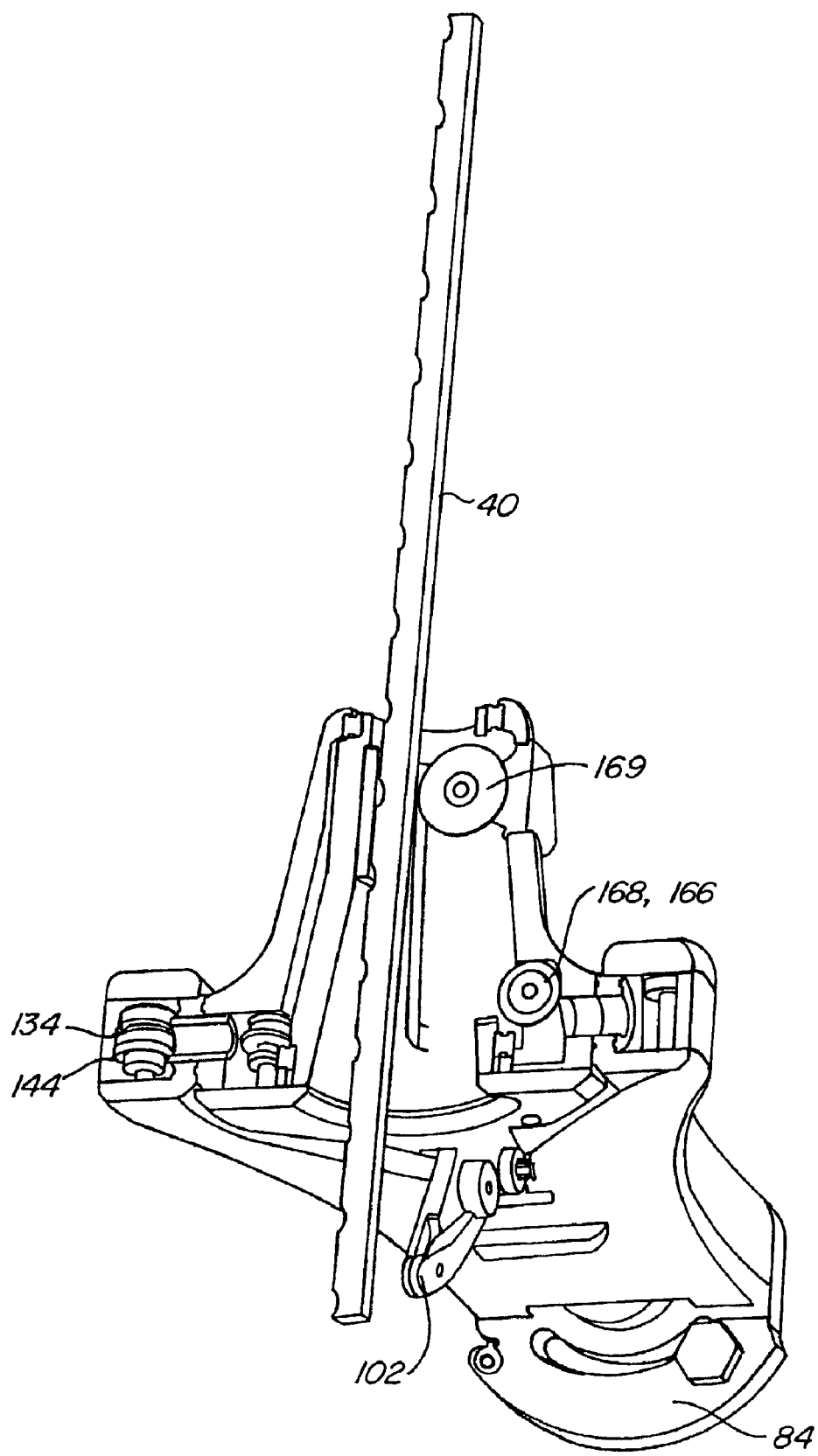
FIGS. 8A and 8B are sectional perspective and front views, respectively, of the mechanical linkage.
Figure 8B:
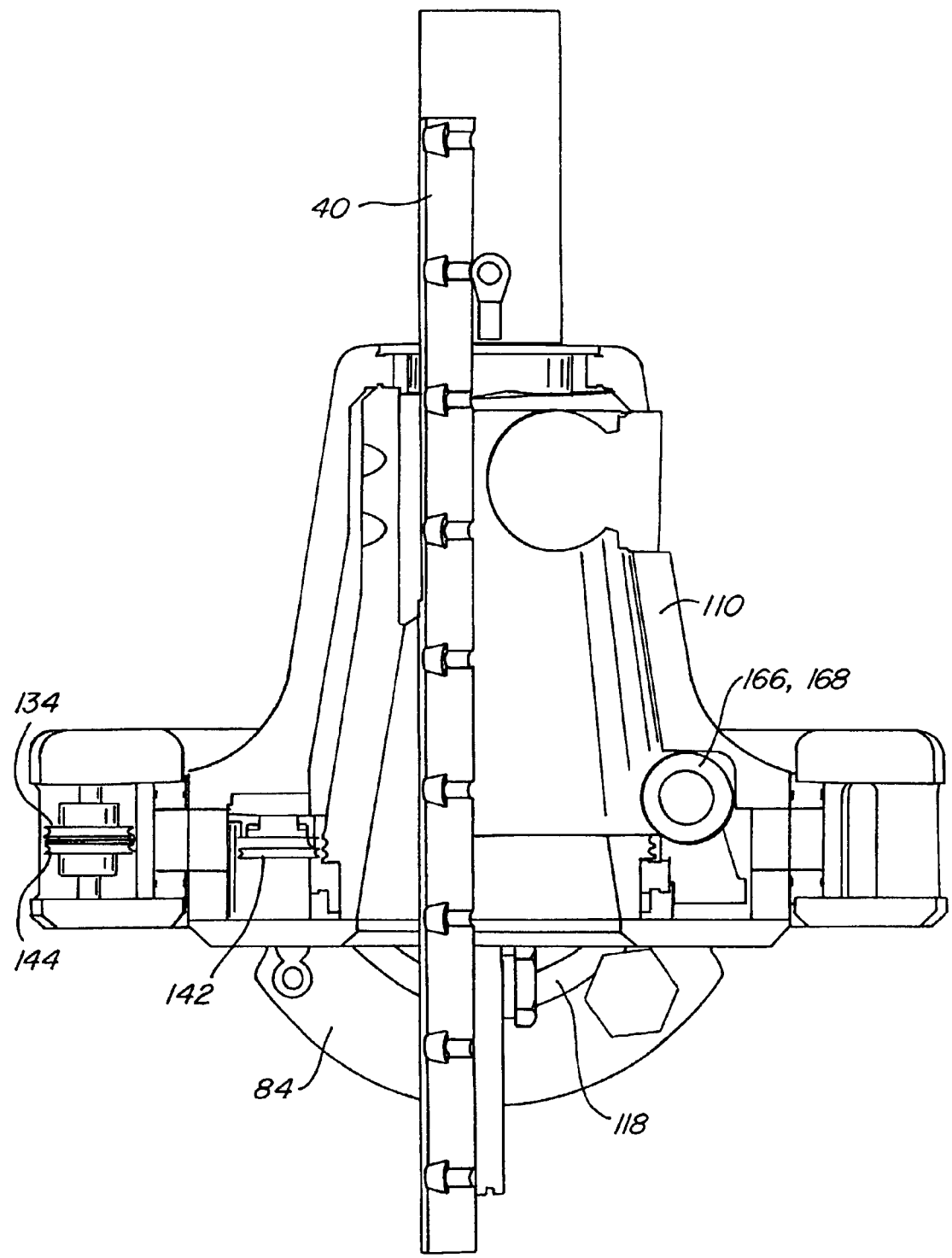

FIGS. 8A and 8B are sectional perspective and front views of the linkage mechanism 38 showing features described above.

Thus, the mechanism of the present invention preferably provides four grounded actuators to provide forces in four degrees of freedom of the tool 18. To make the actuators grounded, cables are used to allow the actuators to output forces to a remote mechanical motion, i.e. the rotated drums or moved linear axis member is located far from the driven pulley, unlike standard capstan drives. The three cables (six ends) routed through the interior of the mechanical linkage and out to the base structure are bent in various ways around idler pulleys and about their lengthwise axes; however, this does not cause significant stretching in the cables. The six ends of the cables are preferably arranged close together close to the pitch axis A so as to minimize bending of the cables. For example, the six cable lengths may be arranged so that their cross sections approximately form a circle around the rotation axis A.

While this invention has been described in terms of several preferred embodiments, it is contemplated that alterations, modifications and permutations thereof will become apparent to those skilled in the art upon a reading of the specification and study of the drawings. For example, the linked members of apparatus 25 may take a number of actual physical sizes and forms while maintaining the disclosed linkage structure. Likewise, other types of gimbal mechanisms or different mechanisms providing multiple degrees of freedom may be used with the drive mechanisms disclosed herein to reduce inertia, friction, and backlash in a system. A variety of devices may also be used to sense the position of an object in the provided degrees of freedom and to drive the object along those degrees of freedom. In addition, the sensor and actuator used in the transducer system having desired play may take a variety of forms. Similarly, other types of couplings may be used to provide the desired play between the object and actuator. Furthermore, certain terminology has been used for the purposes of descriptive clarity, and not to limit the present invention.

What is claimed is:

1. A system, comprising:
   a manipulandum;
   a simulation apparatus including a linkage coupled to the manipulandum, the simulation apparatus being one of a simulated body part and configured to be coupled to a simulated body part; and
   an interface device coupled to the simulation apparatus and configured to be coupled to a host computer, the linkage configured to move based on a control signal associated with the host computer, the interface device being included within one of the host computer and the simulation apparatus.

2. The system of claim 1, wherein the manipulandum is one of a simulated medical instrument and a medical instrument.

3. The system of claim 1, wherein the interface device includes a microprocessor, the interface device being disposed in the simulation apparatus.

4. The system of claim 1, further comprising a barrier between the simulation apparatus and the manipulandum.

5. The system of claim 1, wherein the manipulandum is configured as a laparoscopic tool including a trocar.

6. The system of claim 1, wherein the manipulandum is configured as one of a catheter, a hypodermic needle, a wire, a fiber optic bundle, a stylus, a joystick, a screw driver, a pool cue and a hand grip.

7. The system of claim 1, wherein the manipulandum is one manipulandum from a plurality of manipulandums.

8. The system of claim 1, wherein the simulation apparatus includes
   a ground member;
   a linear axis member coupled to the manipulandum and the linkage;
   an actuator coupled to the ground member; and
   a cable coupled to the at least one actuator and the linkage.

9. The system of claim 1, wherein the simulation apparatus includes
   a ground member;
   a linear axis member coupled to the manipulandum and the linkage;
   at least four actuators coupled to the ground member; and
   at least three cables coupled to the at least four actuators and the linkage.

10. The system of claim 9, wherein the at least four actuators include DC motors.

11. The system of claim 8 comprising at least one sensor configured to sense a movement of at least one of the actuator and the linkage.

12. The system of claim 9, further comprising at least four sensors configured to sense a movement of at least one of the at least four actuators and the linkage.

13. A system, comprising:
   manipulandum;
   a simulation apparatus coupled to the manipulandum, the simulation apparatus comprising:
      a ground member;
      a linkage rotatably coupled to the ground member;
      a linear axis member coupled to the manipulandum and the linkage;
      at least four actuators coupled to the ground member;
      at least one sensor configured to sense a movement of at least one of the at least four actuators and the linkage; and
      at least three cables coupled to the at least four actuators and coupled to the linkage;
   an interface device coupled to the simulation apparatus and a host computer, the
   host computer configured to output a control signal, the linkage configured to move based on the control signal.

14. The system of claim 13, wherein the manipulandum is one of a simulated medical tool and a medical tool.

15. The system of claim 13, wherein the interface device is included within one of the host computer and the simulation apparatus.

16. The system of claim 13, wherein the interface device is separate from the host computer and the simulation apparatus.

17. The system of claim 13, wherein the at least four actuators include DC motors.

18. The system of claim 13, wherein the interface device includes a microprocessor local to simulation apparatus, the interface device being disposed in the simulation apparatus.

19. The system of claim 13, further comprising a barrier between the simulation apparatus and the manipulandum.

20. The system of claim 13, wherein the manipulandum is configured as a laparoscopic tool including a trocar.

21. The system of claim 13, wherein the practice tool is one of a catheter, hypodermic needle, a wire, a fiber optic bundle, a stylus, a joystick, a screw driver, a pool cue and a hand grip.

22. The system of claim 13, wherein the manipulandum is one manipulandum from a plurality of manipulandums.

23. A method, comprising:

receiving an input signal from a sensor, the signal being associated with at least one of a position of a linkage and an input force applied to the linkage, the linkage being coupled between a ground member of a simulation apparatus and a manipulandum, the simulation apparatus being one of a simulated body part and configured to be coupled to a simulated body part; and outputting haptic feedback via an actuator, the actuator being one actuator from a plurality of actuators, the haptic feedback being operative to move the linkage via a plurality of cables coupled between the plurality of actuators and the linkage, the haptic feedback based on the input signal and a control signal received from a host computer.

\* \* \* \* \*